United States Patent [19]

Folkman et al.

[11] Patent Number: 5,290,807
[45] Date of Patent: Mar. 1, 1994

[54] METHOD FOR REGRESSING ANGIOGENESIS USING O-SUBSTITUTED FUMAGILLOL DERIVATIVES

[75] Inventors: Moses J. Folkman, Brookline; Donald Ingber, Boston, both of Mass.

[73] Assignee: Children's Medical Center Corporation, Boston, Mass.

[21] Appl. No.: 917,827

[22] Filed: Jul. 21, 1992

Related U.S. Application Data

[63] Continuation of Ser. No. 811,800, Dec. 19, 1991, abandoned, which is a continuation of Ser. No. 391,980, Aug. 10, 1989, abandoned.

[51] Int. Cl.$^5$ ............................................. A61K 31/335
[52] U.S. Cl. .................... 514/475; 514/231.5; 514/252; 514/278; 514/397; 514/409
[58] Field of Search ............ 549/332; 514/409, 231.5, 514/252, 278, 397, 475

[56] References Cited

U.S. PATENT DOCUMENTS

4,954,496  9/1990  Oku et al. ............................ 549/551

FOREIGN PATENT DOCUMENTS

0325199  7/1989  European Pat. Off. .
2-85272  3/1990  Japan .

OTHER PUBLICATIONS

Chemical Abstracts, vol. 70, No. 9, Mar. 3, 1969, p. 206, Abstract No. 36365g, Columbus, Ohio, US; M. M. Maevskii et al.
Chemical Abstracts, vol. 106, No. 21, May 25, 1987, p. 706, Abstract No. 176153y, Columbus, Ohio, US; JP-A-62 00 476 (Fujisawa Pharmaceutical Co., Ltd.).
Derwent Printout from Dialog of the abstract corresponding to Japanese Kokai Tokkyo Koho No. 58-131978 (1983).
Derwent Printout frm Dialog of the abstract corresponding to Japanese Kokai Tokkyo Koho No. 63-119500 (1988).
S. Taylor, et al., Nature, 297:307 (1982).
J. Folkman et al., Science, 221:719 (1983).
D. Tarbell, et al., J. Am. Chem. Soc. 83:3096 (1961).
O. Mitunobu, Synthesis (1981), 1, pp. 1-28.
I. Sutherland (Ed.), "Compreshensive Organic Chemistry", vol. 2, pp. 4-11, Pergamon Press (1979).
Gimbrone, et al., J. National Cancer Institute, 52:413-419 (1974).
J. Ross, et al., J. Am. Chem. Soc., 78:4675 (1956).
Falk, et al., J. Immunol. Meth., 33:239-247 (1980).
Folkman, et al., Science, 230:1375 (1985).
Chemical Patent Index, Basic Abstracts Journal Section B, Week 8706, Abstract No. 87-040948/06. Abstract of JP-A-476/1987.
J. DiPaolo, et al., Antibiotics Annual, 1958-1959, pp. 541-546.
G. Ruecker, et al., Chemical Abstracts, 77:29f (1972).
The Merck Index, 11th Ed., (1989) pp. 670-671; Compound No. 4199-Fumagillin.

Primary Examiner—John M. Ford
Assistant Examiner—Philip I. Datlow
Attorney, Agent, or Firm—David G. Conlin; David S. Resnick; Gregory D. Williams

[57] ABSTRACT

O-substituted fumagillol derivatives and its salts have an angiogenesis regressing activity are useful for treatment of diseases induced by abnormally stimulated neovascularization.

7 Claims, No Drawings

METHOD FOR REGRESSING ANGIOGENESIS USING O-SUBSTITUTED FUMAGILLOL DERIVATIVES

This is a continuation of application Ser. No. 07/811,880 filed Dec. 19, 1991 now abandoned which is a continuation of application Ser. No. 07/391,980 filed Aug. 10, 1989, now abandoned.

This invention relates to novel O-substituted fumagillol derivatives or salts thereof, which have angiogenesis inhibitory activity and are effective in the treatment and prevention of various inflammatory diseases (rheumatism, psoriasis, etc.), diabetic retinopathy and cancer, among others.

Angiogenesis is deeply concerned in the course of manifestation or progress of various diseases, for example various inflammatory diseases (rheumatism, psoriasis, etc.), diabetic retinopathy, and cancer. Therefore, to inhibit angiogenesis is considered to contribute to the treatment and prevention of such diseases. In fact, several groups of researchers have so far searched for angiogenesis inhibitory substances. As examples, there may be mentioned the study by Taylor et al. [Taylor, S. et al., Nature, 297, 307 (1982)] on the applicability of protamine and the study by Folkman et al. [Folkman, J. et al., Science, 221, 719 (1983)] on the combined use of heparin and cortisone. Furthermore, patent applications have been filed alleging, for example, that ascorbic acid ethers and related compounds (Japanese Kokai Tokkyo Koho No. 58-131978) and the sulfated polysaccharide DS4152 (Japanese Kokai Tokkyo Koho No. 63-119500) show angiogenesis inhibitory activity. However, such substances are not yet fully satisfactory from the activity viewpoint. The advent of compounds superior in activity is waited for.

Accordingly, it is an object of the invention to provide novel compounds having angiogenesis inhibitory activity.

The present inventors searched for and evaluated various compounds in an attempt to achieve the above object and, as a result, found that O-substituted derivatives of fumagillol, a hydrolyzate of fumagillin so far known as an antimicrobial and antiprotozoal agent, have potent angiogenesis inhibitory activity. Based on this finding, they have now completed the present invention. Thus, the invention relates to O-substituted fumagillol derivatives (hereinafter sometimes referred to as compounds (I) for short) of the formula

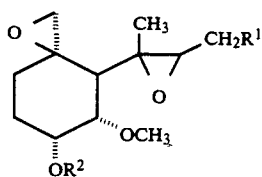

(I)

wherein $R^1$ is a 2-methyl-1-propenyl or isobutyl group which may be substituted and $R^2$ is (1) a substituted alkanoyl group, (2) a substituted aroyl group having at least one substituent selected from the group consisting of $C_{2-6}$ alkyl, amino, halogen, hydroxyl, lower alkoxy, cyano, carbamoyl and carboxyl, (3) an aromatic heterocycle-carbonyl, which may optionally be substituted, (4) a carbamoyl group, which may optionally be substituted, (5) an alkyl group, which may optionally be substituted, (6) a benzenesulfonyl group, which may optionally be substituted, (7) an alkylsulfonyl group, which may optionally be substituted, (8) a sulfamoyl group, which may optionally be substituted, (9) an alkoxycarbonyl group, which may optionally be substituted or (10) a phenoxycarbonyl group, which may optionally be substituted, or salts thereof.

Referring to the above formula, the substituent on the optionally substituted 2-methyl-1-propenyl or isobutyl group represented by $R^1$ includes, among others, hydroxyl, amino, lower ($C_{1-3}$) alkylamino (e.g. methylamino, ethylamino, isopropylamino), di-lower ($C_{1-3}$) alkylamino (e.g. dimethylamino, diethylamino) and a 5- or 6-membered heterocyclic ring containing nitrogen atom (e.g. pyrroridin-1-yl, piperidino, morpholino, piperazin-1-yl, 4-methylpiperozin-1-yl, 4-ethylpiperazin-1-yl), particularly preferred among them are hydroxyl and dimethylamino.

Referring to the above formula, the substituted alkanoyl group represented by $R^2$ includes, among others, alkanoyl groups (preferably containing 1 to 20 carbon atoms; examples in the unsubstituted form: formyl, acetyl, propionyl, isopropionyl, butyryl, pentanoyl, hexanoyl, heptanoyl, octanoyl, nonanoyl, lauroyl, undecanoyl, myristoyl, palmitoyl, stearoyl, arachinoyl, etc.) having at least one, preferably one to three substituents each selected from among amino, lower alkylamino (e.g. methylamino, ethylamino, isopropylamino, etc.), di-(lower alkyl)amino (e.g. dimethylamino, diethylamino, etc.), nitro, halogen (e.g. fluorine, chlorine, bromine, iodine, etc.), hydroxyl, lower alkoxy (e.g. methoxy, ethoxy, etc.), cyano, carbamoyl, carboxyl, lower alkoxycarbonyl (e.g. methoxycarbonyl, ethoxycarbonyl, etc.), carboxy-lower alkoxy (e.g. carboxymethoxy, 2-carboxyethoxy, etc.), phenyl which may optionally be substituted, aromatic heterocyclic group (preferably 5- or 6-membered aromatic heterocyclic group containing one to four hetero atoms each selected from among nitrogen, oxygen, sulfur and so on; e.g. 2-furyl, 2-thienyl, 4-thiazolyl, 4-imidazolyl, 4-pyridyl, etc.) and other substituents. Particularly preferred among them are 3-carboxypropionyl and 4-carboxybutyryl.

As the substituted aroyl group represented by $R^2$, there may be mentioned benzoyl, 1-naphthoyl and 2-naphthoyl each having at least one, preferably one to three substituents each selected from among $C_{2-6}$ lower alkyl, such as ethyl or propyl, amino, halogen (e.g. fluorine, chlorine, bromine, etc.), hydroxyl, lower alkoxy (e.g. methoxy, ethoxy, etc.), cyano, carbamoyl, carboxyl and other substituents. Particularly preferred among them is 2-carboxybenzoyl.

As the substituent or substituents on the optionally substituted aromatic heterocycle-carbonyl group represented by $R^2$, there may be mentioned those substituents mentioned above referring to the substituted aroyl group. Usable as the aromatic heterocycle-carbonyl are 5- or 6-membered ones containing one to four heteroatoms each selected from among nitrogen, oxygen, sulfur and so on. Preferred among others are 2-furoyl, 2-thenoyl, nicotinoyl, isonicotinoyl and imidazole-1-carbonyl.

The carbamoyl group, which may optionally be substituted, represented by $R^2$ includes carbamoyl, mono-substituted carbamoyl and disubstituted carbamoyl. As the substituents, there may be mentioned, for example, lower alkyl (e.g. methyl, ethyl, propyl, butyl, etc.), lower alkanoyl (preferably containing 1 to 6 carbon atoms; e.g. acetyl, propionyl, acryloyl, methacroyl etc.), chloroacetyl, dichloroacetyl, trichloroacetyl, lower alkoxycarbonylmethyl (e.g. methoxycarbonylmethyl, ethoxycarbonylmethyl, etc.), carboxymethyl, amino, phenyl which may optionally be substituted, naphthyl, benzoyl, and substituents forming, together with the carbamoyl nitrogen atom, cyclic amino groups (e.g. pyrrolidin-1-yl, piperidino, morpholino, piperazin-1-yl, 4-methylpiperazin-1-yl, 4-ethylpiperazin-1-yl, 4-phenylpiperazin-1-yl, imidazol-1-yl, etc.). Preferred among them are chloroacetyl, phenyl, benzoyl and the like.

The substituent of carbamoyl further includes halogenated lower alkyl (e.g. 2-chloroethyl, 2-bromoethyl, 3-chloropropyl), di-lower alkylamino-lower alkyl (e.g. 2-dimethylaminoethyl, 2-diethylaminoethyl, 3-dimethylaminopropyl), lower alkanoyloxy-lower alkanoyl (e.g. acetoxyacetyl, propionyloxyacetyl), lower alkanoylthio-lower alkanoyl (e.g. acetylthioacetyl, propionylthioacetyl), lower alkylthio-lower alkanoyl (e.g. methylthioacetyl, ethylthiopropionyl), arylthio-lower alkanoyl (e.g. phenylthioacetyl, naphthylthioacetyl), aromatic heterocyclicthio-lower alkanoyl (e.g. 4-pyridylthioacetyl), 2-pyridylthioacetyl, 2-benzothiazolylthioacetyl, 2-benzoxazolylthioacetyl, 2-benzoimidazolylthioacetyl, 8-quinolylthioacetyl, [1-(2-dimethylaminoethyl)tetrazol]-5-ylthioacetyl, 2-methyl-1,3,4-thiadiazol-5-ylthioacetyl, 1-methyl-2-methoxycarbonyl-1,3,4-triazol-5-ylthioacetyl), N-oxy-2-pyridylthio-lower alkanoyl (e.g. N-oxy-2-pyridylthioacetyl), N-lower alkyl-4-pyridiniothio-lower alkanoyl.halide (e.g. N-methyl-4-pyridinoacetyl.iodide), dilower alkylamino-lower alkanoyl (e.g. dimethylaminoacetyl, diethylaminoacetyl), ammonia-lower alkanoyl.halide (e.g. trimethylammonioacetyl.iodide, N-methylpyrrolidinoacetyl.chloride), aromatic heterocyclic-carbonyl (e.g. 3-furoyl, nicotinoyl, 2-thenoyl), lower alkoxycarbonyl (e.g. methoxycarbonyl, ethoxycarbonyl), phenoxycarbonyl, chloroacetylcarbamoyl, benzoylcarbamoyl, phenylsulfonyl which may have substituent (e.g. benzensulfonyl, toluensulfonyl) and di(lower alkyl)sulfonio-lower alkanoyl.halide (e.g. dimethylsulfonioacetyl.iodide).

As the alkyl group, which may optionally be substituted, represented by $R^2$, there may be mentioned straight or branched $C_{1-20}$ alkyl groups, which may optionally have one to three substituents each selected from among, for example, those substituents mentioned above for the substituted alkanoyl group. Said alkyl group may be epoxidized at any optional position. Methyl, ethyl, benzyl and the like are preferred among others.

As the substituent or substituents on the optionally substituted benzenesulfonyl group, represented by $R^2$, there may be mentioned, for example, lower alkyl (e.g. methyl, ethyl, etc.) and halogen (e.g. fluorine, chlorine, bromine, etc.). One to three such substituents may be present on the benzene ring at any optional position or positions.

As the alkylsulfonyl group, which may optionally be substituted, represented by $R^2$, there may be mentioned, among others, $C_{1-6}$ lower alkylsulfonyl groups, which may have one to three substituents each selected from among, for example, those substituents mentioned above for the substituted alkanoyl group. Preferred among them are methylsulfonyl and ethylsulfonyl.

As the substituent or substituents on the optionally substituted sulfamoyl group represented by $R^2$, there may be mentioned, for example, lower alkyl (e.g. methyl, ethyl, propyl, isopropyl, isobutyl, etc.), phenyl and substituted phenyl. The sulfamoyl group may have either one substituent or two substituents which are the same or different.

As the alkoxycarbonyl group, which may optionally be substituted, represented by $R^2$, there may be mentioned straight or branched lower alkoxycarbonyl groups, which may optionally have one to three substituents each selected from among those substituents mentioned above, for instance. Preferred among them are methoxycarbonyl, ethoxycarbonyl, propoxycarbonyl, butoxycarbonyl, isobutoxycarbonyl, 1-chloroethoxycarbonyl, and the like.

The substituent or substituents on the optionally substituted phenoxycarbonyl group represented by $R^2$ may be the same as those mentioned above for the optionally substituted benzenesulfonyl group. The phenoxy group may have one to three such substituents at any optional position or positions.

In this specification, the substituent or substituents on each optionally "substituted phenyl" group include, among others, lower alkyl (e.g. methyl, ethyl, propyl, butyl, etc.), lower alkoxy (e.g. methoxy, ethoxy, propoxy, etc.), halogen (e.g. fluorine, chlorine, bromine, etc.), haloalkyl (e.g. trifluoromethyl, chloromethyl, bromomethyl, etc.) and nitro. The phenyl ring may have one to five such substituents at any optional position or positions.

In this specification, unless otherwise specified, the term "lower alkyl" or "lower alkyl group" means a straight or branched alkyl group containing 1 to 6 carbon atoms and the term "lower alkoxy" or "lower alkoxy group" means an alkoxy group containing 1 to 6 carbon atoms, prefrably 1 to 3 carbon atoms.

The compounds (I) according to the invention may be used in the form of pharmaceutically acceptable salts if they have an acidic substituent (e.g. carboxyl etc.) or a basic substituent (e.g. amino, lower alkylamino, di-lower alkylamino, etc.). Said pharmaceutically acceptable salts may include salts with inorganic bases, salts with organic bases, salts with inorganic acids, salts with organic acids and salts with basic or acidic amino acids, among others. Available for the formation of such salts are such inorganic bases as alkali metals (e.g. sodium, potassium, etc.) and alkaline earth metals (e.g. calcium, magnesium, etc.), such organic bases as trimethylamine, triethylamine, pyridine, picoline, N,N-dibenzylethylenediamine, ethanolanine, diethanolamine, trishydroxymethylaminomethane and dicyclohexylamine, such inorganic acids as hydrochloric acid, hydrobromic acid, sulfuric acid, nitric acid and phosphoric acid, such organic acids as formic acid, acetic acid, trifluoroacetic acid, oxalic acid, tartaric acid, fumaric acid, maleic acid, methanesulfonic acid, benzenesulfonic acid and p-toluenesulfonic acid, and such basic or acidic amino acids as arginine, lysine, ornithine, aspartic acid and glutamic acid. Among these salts, the salts with bases (i.e. salts with inorganic bases, salts with organic bases and salts with basic amino acids) are those salts in which the carboxyl group contained in a substituent in compounds (I) is involved in the salt formation while, in the salts with acids (i.e. salts with inorganic acids, salts with organic acids and salts with acidic amino acids), an amino, lower alkylamino or di-lower alkylamino group, among others, contained in a substituent in compounds (I) is involved in the salt formation.

The O-substituted fumagillol derivatives in which $R^1$ in formula (I) is a 2-methyl-1-propenyl group can be produced by subjecting fumagillol (Tarbell, D. S. et al., J. Am. Chem. Soc., 83, 3096 (1961)], which is a hydrolyzate of fumagillin produced by microorganisms, to acylation, carbamoylation, alkylation or sulfonylation using an acylating, carbamoylating, alkylating or sulfonylating agent in the manner mentioned below, or by isolating intermediates in such a reaction.

The O-substituted dihydrofumagillol derivatives in which, in formula (I), $R^1$ is an isobutyl group can be produced by subjecting 4',5'-dihydrofumagillol (11), which is obtainable by catalytically reducing fumagillol under ordinary conditions (e.g. using 5% palladium-carbon in a methanol solution; cf. Reference Example 1), to the same reaction as mentioned above.

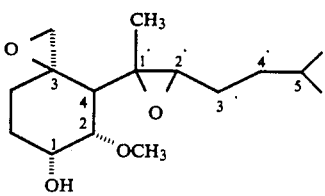
(II)

In cases where $R^2$ is a group inert to catalytic reduction, it is also possible to convert the O-substituted fumagillol derivatives in which $R^1$ is a 2-methyl-1-propenyl group to the O-substituted dihydrofumagillol derivatives in which $R^1$ is an isobutyl group by catalytic reduction.

Those O-substituted fumagillol derivatives of formula (I) in which $R^1$ is a hydroxyl-substituted 2-methyl-1-propenyl or isobutyl group can be produced by subjecting fumagillol whose 6-position hydroxyl may be protected to oxidation for introduction of a hydroxyl group thereinto, and then subjecting the oxidation product, after deprotection of the 6-position hydroxyl as necessary, to acylation, carbamoylation, alkylation or sulfonylation, or by isolating the respective reaction intermediates. In the step of the above-mentioned acylation, carbamoylation, alkylation or sulfonylation, the reaction can proceed advantageously when the hydroxyl group introduced into $R^1$ is protected as necessary.

In cases where $R^2$ is a group inert to oxidation, the O-substituted fumagillol derivatives just mentioned above can be produced also by sujecting those O-sustituted fumagillol derivatives of formula (I) in which $R^1$ is a 2-methyl-1-propenyl or isobutyl group directly to oxidation.

Those O-substituted fumagillol derivatives of formula (I) in which $R^1$ is an animo-, lower alkylamino or di-lower alkylamino-substituted or 5 or 6-membered nitrogen-containing heterocycle-substituted 2-methyl-1-propenyl or isobutyl group can be produced by subjecting the abovementioned fumagillol derivatives having a hydroxyl group introduced in the 4-position side chain moiety, -methyl-1-propenyl or isobutyl group, by the above-mentioned oxidation, the 6-position hydroxyl of which may be protected, to amination and then subjecting the amination product, after deprotection of the 6-position hydroxyl, to acylation, carbamoylation, alkylation or sulfonylation, or by isolating the respective reaction intermediates. In the step of the above-mentioned acylation, carbamoylation, alkylation or sulfonylation, the reaction can proceed with advantage when the amino, lower alkylamino or nitrogen-containing heterocyclic group introduced into $R^1$ is protected as necessary.

In cases where $R^2$ is a group inert or resistant to amination, the O-substituted fumgillol derivatives just mentioned above can be produced also by subjecting an O-substituted fumagillol derivative of formula (1) in which $R^1$ is a hydroxyl-substituted 2-methyl-1-propenyl or isobutyl group to amination.

Those O-substituted fumagillol derivatives of formula (I) in which $R^1$ is a hydroxyl-, amino-, lower alkylamino-, di-lower alkylamino- or 5- or 6-membered nitrogen-containing heterocycle-substituted isobutyl group can be produced by subjecting a fumagillol derivative having a hydroxyl, amino, lower alkylamino, di-lower alkylamino or 5- or 6-membered nitrogen-containing heterocyclic group introduced in the 4-position side chain moiety 2-methyl-1-propenyl group, the 6-position hydroxyl of which may be protected, to catalytic reduction and then subjecting the reduction product, after deprotection of the 6-position hydroxyl as necessary, to acylation, carbamoylation, alkylation or sulfonylation, or by isolating the respective reaction intermediates. In the step of acylation, carbamoylation, alkylation or sulfonylation, the reaction can proceed with advantage when the hydroxyl, amino, lower alkylamino or nitrogen-containing heterocyclic group in $R^1$ is protected as necessary.

In cases where $R^2$ is a group inert to catalytic reduction, the O-substituted fumagillol derivatives just mentioned above can be produced also by sujecting those O-sustituted fumagillol derivatives of formula (1) in which $R^1$ is a 3-hydroxy-2-methyl-1-propenyl group directly to catalytic reduction.

The protection and deprotection of the 6-position hydroxyl and of the hydroxyl, amino, lower alkylamino and nitrogen-containing heterocycle in $R^1$ can be carried out by an appropriate per se known method [cf. Greene, T. W., "Protective Groups in Organic Synthesis", John Wiley & Sons, New York (1981)].

In cases where such a substituent as amino, hydroxyl or carboxyl is present in the acylating, carbamoylating, alkylating or sulfonylating agnet, such substituent should preferably be protected by an appropriate protective group selected on the basis of the stability of the product. As examples of preferred protective groups, there may be mentioned 4-nitrobenzyloxycarbonyl and 2-trimethylsilylethoxycarbonyl for amino protection, 4-nitrobenzyl and t-butyldimethylsilyl for hydroxyl protection, and 4-nitrobenzyl for carboxyl protection. Deprotection can be effected by a conventional method, for example by catalytic reduction or reaction with the fluoride ion. In the case of carbamoylation or alkylation, it is also possible to use a lower alkyl group, such as methyl or ethyl, as the carboxyl-protecting group so that postreaction deprotection can be effected by hydrolysis under mild alkaline conditions.

1) Acylation

Said acylation is carried out by bringing fumagillol or dihydrofumagillol (hereinafter referred to as "starting alcohol") into contact with an activated, reactive derivative of a carboxylic acid, for example an acid anhydride or an acid halide (e.g. acid chloride, acid bromide, etc.).

Thus, the reaction proceeds according to the equation:

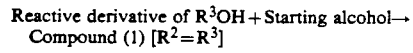

In the above equation, $R^3$ is (1) a substituted alkanoyl group, (2) a substituted aroyl group having at least one substituent selected from the group consisting of $C_{2-6}$ alkyl, amino, halogen, hydroxyl, lower alkoxy, cyano, carbamoyl and carboxyl, or (3) an aromatic heterocycle-carbonyl group, which may optionally be substituted, as defined with respect to $R^2$.

Said reactive derivative of carboxylic acid is used generally in an amount of about 1 to 10 moles, preferably 1 to 5 moles, per mole of the starting alcohol.

The reaction is carried out generally in the presence of a base. Usable as said base are tertiary amines, such as diisopropylethylamine, triethylamine, pyridine and N,N-dimethylaminopyridine, alkali metal hydrogen carbonates, such as sodium hydrogen carbonate and potassium hydrogen carbonate, alkali metal carbonates, such as potassium carbonate and sodium carbonate, alkali metal hydrides, such as sodium hydride and potassium hydride, and organometals, such as butyllithium and lithium diisopropylamide. The base is used generally in an amount of about 1 to 10 moles per mole of the starting alcohol.

This reaction is carried out generally in an organic solvent which will not interfere with the reaction. Usable as such inert organic solvent are, for example, amides, such as dimethylformamide and dimethylacetamide, halogenated hydrocarbons, such as dichloromethane, chloroform and 1,2-dichloroethane, ethers, such as diethyl ether, tetrahydrofuran and dioxane, esters, such as methyl acetate, ethyl acetate, isobutyl acetate and methyl propionate, nitriles, such as acetonitrile and propionitrile, nitro compounds, such as nitromethane and nitroethane, ketones, such as acetone and methyl ethyl ketone, and aromatic hydrocarbons, such as benzene and toluene. These may be used either alone or in the form of a mixture of two or more of them mixed together in an appropriate ratio. When a tertiary amine is used as the base, said amine as such may serve also as a solvent.

The optimal reaction temperature may vary depending on the carboxylic acid derivative, base and solvent and amounts thereof, among others but can be found within the range of $-80°$ C. to $100°$ C., preferably $0°$ C. to room temperature (the term "room temperature" means a temperature of about $20°$ to $35°$ C.; unless otherwise specified, the same shall apply hereinafter). The reaction time required is about 30 minutes to 5 days.

2) Alkylation

Said alkylation is effected by reacting the starting alcohol with an alkylating agent, for example an alkyl halide or a dialkyl sulfate (e.g. dimethyl sulfate, diethyl sulfate, etc.), representable by the formula $R^4Y$ [wherein $R^4$ is (5) an alkyl group, which may optionally be substituted, as defined with respect to $R^2$, and Y is a leaving group (e.g. halogen (chlorine, bromine, iodine, etc.))]. Said alkylating agent is used generally in an amount of about 1 to 5 moles per mole of the starting alcohol.

This reaction is carried out generally in the presence of a base. Usable as said base are, for example, those alkali metal hydrogen carbonates, alkali metal carbonates, alkali metal hydrides and organometals mentioned above. The base is used generally in an amount of about 1 to 5 moles per mole of the starting alcohol.

This reaction is carried out generally in an organic solvent which will not interfere with the reaction. Usable as such inert organic solvent are those amides, halogenated hydrocarbons, ethers, esters, nitriles, nitro compounds, ketones and aromatic hydrocarbons mentioned above. These may be used either singly or in the form of a mixture of two or more of them mixed together in an appropriate ratio.

The optimal reaction temperature may depend on the alkylating agent, base and solvent and amounts thereof but is generally within the range of $-80°$ C. to $100°$ C., preferably from $0°$ C. to room temperature. The reaction time amounts to about 20 minutes to 5 days.

3) Carbamoylation

The carbamoylation reaction for the introduction of a monosubstituted carbamoyl group is carried out generally by bringing the starting alcohol into contact with an isocyanate, for example according to the following equation:

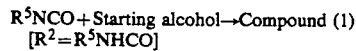

$$[R^2 = R^5NHCO]$$

In the above equation, $R^5$ is lower alkyl, lower alkanoyl, chloroacetyl or the like substituent on the optionally substituted carbamoyl represented by $R^2$. Said isocyanate is used generally in an amount of about 1 to 5 moles per mole of the starting alcohol.

This reaction is carried out generally in the presence of a base. Usable as said base are, for example, those tertiary amines, alkali metal hydrogen carbonates, alkali metal carbonates, alkali metal hydrides and organometals mentioned above. The level of addition of said base is generally about 1 to 5 moles per mole of the starting alcohol.

This reaction is carried out generally in an organic solvent which will not interfere with the reaction. Usable as such inert organic solvent are those amides, halogenated hydrocarbons, ethers, esters, nitriles, nitro compounds, ketones and aromatic hydrocarbons mentioned above. These may be used either singly or in the form of a mixture or two or more of them mixed together in an appropriate ratio. When a tertiary amine is used as the base, said tertiary amine as such may also serve as a solvent.

The optimal reaction temperature may depend on the isocyanate, base and solvent and amounts thereof but is generally within the range of $-80°$ C. to $100°$ C., preferably from $0°$ C. to room temperature. The reaction time required amounts to about 1 hour to 5 days.

Among the monosubstituted carbamoyl group-containing compounds thus obtained, those compounds having a chloroacetylcarbamoyl or trichloroacetylcarbamoyl group, for instance, may be converted to the corresponding compounds having an unsubstituted carbamoyl group by eliminating the chloroacetyl or trichloroacetyl group by a conventional method (e.g. under basic conditions at room temperature or with heating).

Said carbamoylation may also be effected by reacting the starting alcohol with a carbamoyl halide.

Said carbamoyl halide is used generally in an amount of about 1 to 5 moles per mole of the starting alcohol.

This reaction is carried out generally in the presence of a base. Usable as the base are those tertiary amines, alkali metal hydrogen carbonates, alkali metal carbonates, alkali metal hydrides and organoalkali metals mentioned above. The level of addition of said base is generally about 1 to 5 moles per mole of the starting alcohol.

This reaction is carried out generally in an organic solvent which will not interfere with the reaction. Usable as such inert organic solvent are those amides, halogenated hydrocarbons, ethers, esters, nitriles, nitro compounds, ketones and aromatic hydrocarbons mentioned above. These may be used either singly or in the form of a mixture, in an appropriate mixing ratio, of two or more of them. When a tertiary amine is used as the base, said tertiary amine as such may also serve as a solvent.

The optimal reaction temperature may vary depending on the carbamoyl halide, base and solvent and amounts thereof. Generally, however, the reaction is carried out at a temperature from about 0° C. to a temperature approximately equal to the refluxing temperature of the reaction medium, preferably from about 25° C. to the refluxing temperature.

Further, said carbamoylation can be effected by reacting the starting alcohol with a chloroformate ester (e.g. phenyl chloroformate, ethyl chloroformate, isobutyl chloroformate, 1-chloroethyl chloroformate, etc.) or 1,1-carbonyldiimidazole and then reacting the resulting active ester with a primary or secondary amine. Said chloroformate ester, 1,1-carbonyldiimidazole or amine is used generally in an amount of about 1 to 5 moles per mole of the starting alcohol.

In the process mentioned just above, the reaction of the starting alcohol with a chloroformate ester is carried out generally in the presence of a base. Usable as said base are those tertiary amines, alkali metal hydrogen carbonates, alkali metal carbonates, alkali metal hydrides and organoalkali metals mentioned above. The level of addition of the base is generally about 1 to 5 moles per mole of the starting alcohol.

This reaction is carried out generally in an organic solvent which will not interfere with the reaction. Usable as such inert organic solvent are the amides, halogenated hydrocarbons, ethers, esters, nitriles, nitro compounds, ketones and aromatic hydrocarbons mentioned above. These may be used either singly or in the form of a mixture, in an appropriate mixing ratio, of two or more of them. The optimal reaction temperature may vary depending on species of chloroformate ester, base, amine and solvent and amounts thereof, among others. Generally, however, the reaction is carried out at a temperature from −20° C. to the refluxing temperature of the reaction medium, preferably at a temperature of 0° C. to 50° C. The active esters obtainable as intermediates are also included within the scope of the objective compounds (I) of the invention.

Among the compounds having a monosubstituted carbamoyl group, those having a substituted lower alkanoylcarbamoyl group can be produced also by reacting a corresponding compound having a chloroacetylcarbamoyl group with a nucleophilic reagent.

The nucleophilic reagent to be used is a lower carboxylic acid, lower thiocarboxylic acid, thiol, amine or the like, or a metal salt thereof.

This reaction is generally carried out in an organic solvent which will not interfere with the reaction. The above-mentioned saturated aliphatic hydrocarbons, alcohols, amides, halogenated hydrocarbons, ethers, esters, nitriles, nitro compounds, ketones and aromatic hydrocarbons, for instance, can be used as such organic solvent inert to the reaction. These may be used either singly or in the form of a mixture of two or more in an appropriate mixing ratio.

Generally, this reaction is carried out in the presence of a base. Usable as said base are, for example, the above-mentioned tertiary amines, alkali metal hydrogen carbonates, alkali metal carbonates, alkali metal hydrides and organoalkali metal compounds. The base is added to the reaction system generally in an amount of about 1 to 5 moles per mole of the starting material.

The optimal reaction temperature may vary depending on the nucleophilic reagent, base and solvent, the quantities thereof and other factors. Generally, however, the reaction is carried out at −80° C. to 100° C., preferably at 0° C. to room temperature. The reaction period is about 20 minutes to 5 days.

4) Sulfonylation

The sulfonylation is effected by reacting the starting alcohol with an activated sulfonic acid derivative such as a sulfonic anhydride or a sulfonic halide (e.g. sulfonyl chloride, sulfonyl bromide, etc.), or an activated sulfamic acid derivative such as a sulfamoyl halide (e.g. sulfamoyl chloride, sulfamoyl bromide, etc.).

Thus, the above process may be illustrated by the following equation:

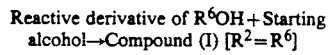

Reactive derivative of $R^6OH$ + Starting alcohol → Compound (I) [$R^2 = R^6$]

In the above equation, $R^6$ is (6) a benzenesulfonyl group, which may optionally be substituted, (7) an alkylsulfonyl group, which may optionally be substituted or (8) a sulfamoyl group, which may optionally be substituted, as defined with respect to $R^2$.

Said reactive derivative of sulfonic acid is used generally in an amount of about 1 to 5 moles per mole of the starting alcohol.

This reaction is carried out generally in the presence of a base. Usable as said base are those tertiary amines, alkali metal hydrogen carbonates, alkali metal carbonates, alkali methal hydrides and organometals mentioned above. The level of addition thereof is generally about 1 to 10 moles per mole of the starting alcohol.

This reaction is carried out generally in an organic solvent which will not interfere with the reaction. Usable as such inert organic solvent are those amides, halogenated hydrocarbons, ethers, esters, nitriles, nitro compounds, ketones and aromatic hydrocarbons mentioned above. These may be used either singly or in the form of a mixture of two or more of them mixed together in an appropriate mixing ratio. When a tertiary amine is used as the base, said tertiary amine as such may serve also as a solvent.

The optimal reaction temperature may vary depending on the sulfonic or sulfamic acid derivative, base and solvent and amounts thereof. Generally, however, the reaction is carried out at −80° C. to 100° C., preferably at 0° C. to room temperature. the reaction time amounts to about 10 minutes to 5 days.

5) Oxidation

Said oxidation is effected by reacting an oxidizing agent with fumagillol, whose 6-position hydroxyl may be protected, or an O-substituted fumagillol derivative of formula (I) in which $R^1$ is a substituted or unsubstituted 2-methyl-1-propenyl or isobutyl group and the 6-position hydroxyl of which may be protected.

Usable oxidizing agents are selenium dioxide, osmium tetroxide, aqueous hydrogen peroxide, organic peroxides (e.g. t-butyl hydroperoxide etc.), organic peracids (e.g. performic acid, peracetic acid, trifluoroperacetic acid, perbenzoic acid, m-chloroperbenzoic acid, etc.) and so forth. It is also possible to use two or more of these in combination in an appropriate mixing ratio. Generally, the oxidizing agent is used in an amount of about 1 to 5 moles per mole of the starting material.

This reaction is generally carried out in a solvent which will not interfere with the invention. Useful examples of such solvent inert to the reaction are water, saturated aliphatic hydrocarbons, such as hexane, heptane, etc., alcohols, such as methanol, ethanol, etc., and the above-mentioned halogenated hydrocarbons, ethers and aromatic hydrocarbons. These may be used either singly or in the form of a mixture of two or more of them in an appropriate mixing ratio.

The optimal reaction temperature may vary depending on the oxidizing agent and solvent, the quantities thereof and other factors. Generally, however, the reaction is carried out at −80° C. to 100° C., preferably at 0° C. to room temperature. The reaction period is about 20 minutes to 5 days.

6) Amination

The amination is conducted for conversion of the hydroxyl group of the fumagillol derivatives having a hydroxyl group introduced in the 4-position side chain, 2-methyl-1-propenyl or isobutyl group, as a result of the above oxidation reaction, the 6-position hydroxyl of which may be protected, or of those O-substituted fumagillol derivatives of general formula (I) in which $R^1$ is a hydroxyl-substituted 2-methyl-1-propenyl or isobutyl group by the method of converting hydroxyl directly to amino by taking advantage of the Mitunobu reaction (cf. Mitunobu, O., *Synthesis*, 1981, 1) which uses an imide, such as phthalimide or succinimide, the method which comprises converting said hydroxyl to methanesulfonyloxy or toluenesulfonyloxy and then convering the latter to an amino, lower alkylamino, di-(lower alkyl)amino or nitrogen-containing heterocyclic group by reaction with ammonia or the corresponding amine, or some other appropriate method.

For the reaction of the sulfonyloxy derivative with ammonia or an amine, aqueous ammonia, gaseous ammonia or liquid ammonia may be used as ammonia and the amine to be used is a primary amine (e.g. methylamine, ethylamine, isopropylamine, etc.), a secondary amine (e.g. dimethylamine, diethylamine, etc.), or a 5- or 6-membered nitrogen-containing heterocyclic compound (e.g. pyrzolidine, piperidine, morpholine, piperazine, N-methylpiperazine, N-ethylpiperazine, etc.).

Generally, this reaction is carried out using ammonia or said amine in an amount of about 1 to 20 moles, preferably 2 to 10 moles per mole of the starting material in a solvent which will not adversely affect the reaction. The ammonia or amine itself may be used as the solvent. Useful as the solvent which will not adversely affect the reaction are, for example, water and such saturated alipahtic hydrocarbons, alcohols, amides, halogenated hydrocarbons, ethers, esters, nitriles, nitro compounds, ketones and aromatic hydrocarbons as mentioned above. These may be used either singly or in the form of a mixture of two or more in an appropriate mixing ratio.

This reaction may also be carried out in the presence of a base, such as an alkali metal hydrogen carbonate or an alkali metal carbonate. Those alkali metal hydrogen carbonates and alkali metal carbonates mentioned above referring to the alkylation can be used also for this reaction.

The optimal reaction temperature may vary depending on the reactant (ammonia or amine), base and solvent, the quantities thereof and other factors. Generally, however, the reaction is carried out at −80° C. to 100° C., preferably at 0° C. to room temperature. The reaction period is about 20 minutes to 5 days.

It is also possible to N-alkylate the amino or lower alkylamino introduced by the above-mentioned method according to a per se known method (cf. Sutherland, I. O. (ed.), "Comprehensive Organic Chemistry", vol. 2, pages 4–11, Pergamon Press (1979)] to give those fumagillol derivatives which have a lower alkylamino or di-(lower alkyl)amino group introduced in the 4-position side chain, 2-methyl-1-propenyl or isobutyl group, and whose 6-position hydroxyl may be protected or those O-substituted fumagillol derivatives of general formula (1) in which $R^1$ is a lower alkylamino- or di-(lower alkyl)amino-substituted 2-methyl-1-propenyl or isobutyl group.

The O-substituted fumagillol derivatives (1) thus produced can be isolated by per se known means of separation and purification (e.g. chromatography, crystallization) or by other appropriate means.

The compounds (I) have asymmetric centers within their molecules and accordingly are optically active. Their absolute configuration comes from the starting material fumagillol. Therefore, it is to be noted that the compounds (I) have the same absolute configuration that fumagillol has.

The compounds according to the invention exhibit angiogenesis inhibitory activity and are useful as therapeutic and prophylactic agents for various inflammatory diseases (rheumatism, psoriasis)., diabetic retinopathy, or cancer. They can be safely administered either orally or nonorally as such or in the form of pharmaceutical preparations [e.g. tablets, capsules (inclusive of soft capsules and microcapsules), solutions, injections, suppositories] prepared by admixing with per se known pharmaceutically acceptable carriers or excipients or the like. The dose may vary depending on the target of administration, route of administration, symptoms and other factors. Generally, however, in adults, they are used, for example, at a dose of about 0.1 mg/kg to 40 mg/kg body weight, preferably about 0.5 mg/kg to 20 mg/kg body weight.

EXPERIMENTAL EXAMPLE 1

The product compounds (I) obtained in the examples given below were evaluated for angiogenesis inhibitory activity by the rat cornea micropocket method. The data obtained are summarized in the table given below.

Method of measurement

Essentially the method of Gimbrone et al. (*J. National Cancer Institute*, 52, 413–419 (1974)] was followed. Thus, adult male Sprague-Dawley rats (11 to 16 weeks of age) were anesthetized with nembutal and locally anesthetized by instillation of xylocaine eyedrops onto the eyeball. The cornea was incised to a length of about 2 mm at about 2 mm inside from the corneal circumference by means of an injection needle, and a sustained release pellet containing basic fibroblast growth factor (bFGF; bovine brain-derived, purified product; R & D) and a sustained release pellet containing the test sample were inserted side by side into the incision so that the bFGF pellet was located on the central side in the cornea. In the control group, the bFGF pellet and a sample-free pellet were inserted into the cornea. After 7 days and after 10 days, the cornea was observed under a stereoscopic microscope. When the sample administration result -ed in retardation or reduction of bFGF-induced angiogenesis, the sample was judged to have inhibitory activity.

The sustained release pellets were prepared in the following manner. An ethylene-vinyl acetate copolymer (Takeda Chemical Industries) was dissolved in dichloromethane to a concentration of 8%. A 3-μl portion of the solution was air-dried on a glass dish, an aqueous solution of bFGF (250 ng) was then placed thereon and air-dried and, finally 3 μl of the above ethylene-vinyl acetate copolymer solution was placed further thereon and air-dried to give a laminate consisting of two copolymer layers and a bFGF layer sandwiched therebetween. This sandwich sheet was made round into a bFGF pellet. The test sample pellets were prepared by dissolving each sample in ethanol in a concentration of 20 μg/2 μl, mixing the solution (2 μl) with 6 μl of an ethylene-vinyl acetate copolymer solution, air-drying the mixed solution on a glass dish and making the thus-obtained sheet round.

TABLE

| Angiogenesis inhibitory activity | | |
|---|---|---|
| Example | Inhibition rate | Judgment |
| 2 | 6/6 | + |
| 4 | 6/7 | + |
| 5 | 8/8* | + |
| 6 | 6/7 | + |
| 8 | 6/6* | + |
| 11 | 9/9* | + |
| 14 | 4/8 | ± |
| 17 | 7/8* | + |
| 18 | 7/7 | + |
| 20 | 3/4 | + |
| 21 | 4/4 | + |
| 22 | 5/8 | ± |
| 23 | 6/8 | + |
| 24 | 5/12 | ± |
| 25 | 6/8 | + |
| 26 | 6/6 | + |
| 27 | 3/7 | ± |
| 28 | 11/11 | + |
| 29 | 7/7 | + |
| 30 | 4/8 | ± |
| 31 | 5/6 | + |
| 32 | 9/12 | + |
| 33 | 4/6 | ± |
| 34 | 4/4 | + |
| 35 | 4/8 | ± |
| 37 | 11/11 | + |
| 38 | 13/15 | + |
| 39 | 8/8 | + |
| 40 | 6/6 | + |
| 41 | 2/4 | ± |
| 42 | 7/7 | + |
| 43 | 7/7 | + |
| 44 | 7/7 | + |
| 45 | 8/13 | ± |
| 46 | 7/10 | + |
| 49 | 4/5 | + |
| 51 | 7/14 | ± |
| 52 | 6/8 | + |
| 53 | 8/8 | + |
| 54 | 5/5 | + |
| 56 | 4/7 | ± |
| 57 | 6/6 | + |
| 58 | 6/6 | + |
| 60 | 4/6 | ± |
| 61 | 7/7 | + |
| 62 | 7/7 | + |
| 63 | 6/6 | + |
| 64 | 5/5 | + |
| 65 | 8/8 | + |
| 67 | 5/5 | + |
| 69 | 6/6 | + |
| 70 | 5/5 | + |
| 75 | 8/8 | + |

*Judged after 7 days. Others judged after 10 days.

In the above table, the inhibition rate is the ratio of the number of rats in which angiogenesis inhibitory activity was observed to the number of rats tested.

EXAMPLES

The following reference examples and examples are fur,--her illustrative of the present invention but are by no means limitative of the scope of the invention.

In the following reference examples and examples, elution in column chromatography (the eluent being given in the parentheses) was performed under TLC (thin layer chromatography) observation. In TLC observation, Merck kieselgel 60F$_{250}$ (70-230 mesh) was used for preparing TLC plates and the solvent used as the eluent in column chromatography was used also as the developing solvent. For detection, a UV detector or coloration with phosphomolybdic acid, for example, was used. Merck kieselgel 60 (70-230 mesh) was used also as the column packing silica gel. Each NMR spectrum is a proton NMR ($^1$H-NMR) spectrum measured on a Varian model Gemini 200 NMR spectrometer with tetramethylsilane as an internal or external standard and reported in terms of δ values in PPM.

In the reference examples and examples, the following abbreviations are used:

s: singlet; br: broad; d: doublet; dd: double doublet; ddd: doublet doublet doublet; t: triplet; q: quartet; m: multiplet; ABq: AB quartet; J: coupling constant; Hz: hertz; CDCl$_3$: deuteriochloroform; d$_6$-DMSO: deuterated dimethyl sulfoxide; %: % by weight.

In the following reference examples and examples, the term "room temperature" means about 15°-25° C. The melting point and temperature data are all given on the Celsius scale.

REFERENCE EXAMPLE 1

Dihydrofumagillol

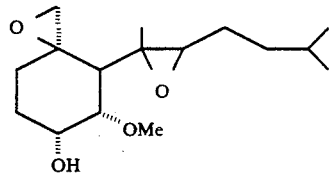

A solution of fumagillol (1.12 g) in ethanol (13 ml) was subjected to catalytic reduction at atmospheric pressure and room temperature for 1 hour, using 5% palladium-on-carbon (120 mg) as the catalyst. The reaction mixture was filtered, the filtrate was concentrated under reduced pressure, and the residue was purified by silica gel chromatography (eluent: n-hexane-ethyl acetate=2:1) to give 871 mg (77% yield) of dihydrofumagillol, a compound described in *J. Am. Chem. Soc.*, 78, 4675 (1956).

EXAMPLE 1

O-(3-Carboxypropionyl)fumagillol

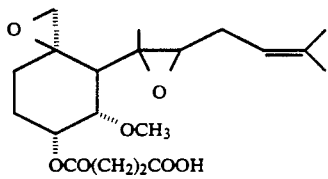

To a solution of fumagillol (240 mg) and dimethylaminopyridine (100 mg) in anhydrous pyridine (1 ml) was added succinic anhydride (250 mg) and the mixture was stirred at room temperature for 3 days. The reaction mixture was concentrated under reduced pressure, and the residue was dissolved in ethyl acetate and washed with water. Then, the organic layer was extracted with saturated aqueous sodium hydrogen carbonate solution. The water layer was adjusted to pH 4 with diluted hydrochloric acid and reextracted with ethyl acetate. The extract was dried over anhydrous magnesium sulfate and the solvent was distilled off under reduced pressure to give colorless, syrupy O-(3-carboxypropionyl)fumagillol (252 mg) (78% yield).

$^1$H-NMR (CDCl$_3$) δ: 1.08 (1H, m), 1.20 (3H, s), 1.65 (3H, s), 1.75 (3H, s), 1.6–2.2 (5H, m), 2.39 (1H, m), 2.56 (1H, d, J=4.2 Hz) 2.65 (5H, m), 2.98 (1H, d, J=4.2 Hz), 3.40 (3H, s), 3.63 (1H, dd, J=11.2 Hz, J=2.8 Hz), 5.22 (1H, m) 5.68 (1H, br s), 7.10 (br s).

EXAMPLE 2

Sodium salt of O-(3-carboxypropionyl)fumagillol

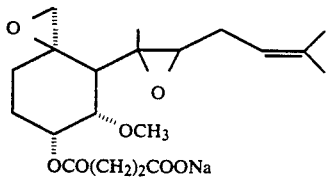

To O-(3-carboxypropionyl)fumagillol (612 mg) was added water (2 ml), followed by portionwise addition of sodium hydrogen carbonate (135 mg) for dissolving the starting material. The solvent was then distilled off under reduced pressure to give colorless, crystalline sodium salt of O-(3-carboxypropionyl)fumagillol (614 mg) (95% yield).

m.p.: gradual decomposition above 120° C.

$^1$H-NMR (D$_2$O) δ: 1.08 (1H, m), 1.23 (3H, s), 1.67 (3H, s), 1.78 (3H, s), 1.6–2.7 (10H, m), 2.77 (1H, d, J=3.8 Hz), 2.90 (1H, t, J=6.2 Hz), 3.10 (1H, d, J=3.8 Hz), 3.41 (3H, s), 3.85 (1H, dd, J=11.0 Hz, J=2.6 Hz), 5.27 (1H, m), 5.62 (1H, br s).

EXAMPLE 3

O-(4-Carboxybutanoyl)fumagillol

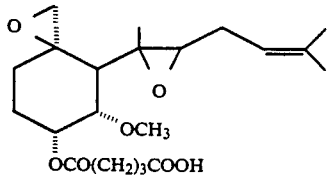

In the same manner as in Example 1, fumagillol (200 mg) was reacted with glutamic anhydride (260 mg) with stirring at room temperature for 24 hours to give colorless, syrupy O-(4-carboxybutanoyl)fumagillol (235 mg) (84%

$^1$H-NMR (CDCl$_3$) δ: 1.08 (1H, m), 1.21 (3H, s), 1.65 (3H, s), 1.75 (3H, s), 1.7–2.6 (12H, m), 2.58 (1H, d, J=4.2 Hz), 2.63 (1H, t, J=6.4 Hz), 2.99 (1H, d, J=4.2 Hz), 3.43 (3H, s), 3.65 (1H, dd, J=11.0 Hz, J=2.6 Hz), 5.20 (1H, m), 5.67 (1H, br s), 8.60 (1H, br s).

EXAMPLE 4

Sodium salt of O-(4-carboxybutanoyl)fumagillol

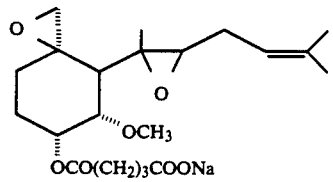

In the same manner as in Example 2, O-(4-carboxybutanoyl)fumagillol (604 mg) was treated with sodium hydrogen carbonate (128 mg) to give colorless, crystalline sodium salt of O-(4-carboxybutanoyl)fumagillol (565 mg) (89% yield).

m.p.: gradual decomposition above 120° C.

$^1$H-NMR (D$_2$O) δ: 1.10 (1H, m), 1.23 (3H, s), 1.67 (3H, s), 1.77 (3H, s), 1.7–2.55 (12H, m), 2.78 (1H, d, J=3.4 Hz), 2.88 (1H, t, J=6.4 Hz), 3.09 (1H, d, J=3.4 Hz), 3.41 (3H, s), 3.84 (1H, dd, J=11.2 Hz, J=2.8 Hz), 5.28 (1H, m), 5.64 (1H, br s).

EXAMPLE 5

O-Carboxymethoxyacetylfumagillol

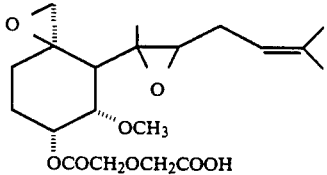

In the same manner as in Example 1, fumagillol (205 mg) was reacted with diglycollic anhydride (255 mg) with stirring at room temperature for 20 hours to give colorless, syrupy O-carboxymethoxyacetylfumagillol (205 mg) (71% yield).

$^1$H-NMR (CDCl$_3$) δ: 1–10 (1H, m), 1.21 (3H, s), 1.63 (3H, s), 1.72 (3H, s), 1.6–2.6 (8H, m), 2.94 (1H, d, J=4.2 Hz),3.41 (3H, s), 3.63 (1H, dd, J=11.2 Hz, J=2.8 Hz), 4.25 (2H, s), 4.30 (2H, s), 5.21 (1H, m), 5.73 (1H, br s), 8.22 (1H, br s).

EXAMPLE 6

O-(2-Carboxybenzoyl)fumagillol

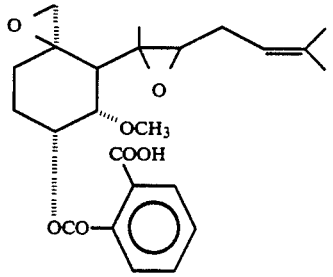

In the same manner as in Example 1, fumagillol (187 mg) was reacted with phthalic anhydride (147 mg) with stirring at room temperature for 3 days. Purification by silica gel column chromatograpy (ethyl acetate) gave colorless, powdery O-(2-carboxybenzoyl)fumagillol (190 mg) (67% yield).

¹H-NMR (CDCl₃) δ: 1.08 (1H, m), 1.24 (3H, s), 1.68 (3H, s), 1.77 (3H, s), 1.9-2.5 (5H, m), 2.35 (1H, d, J=11.6 Hz),2.60 (1H, d, J=4.1 Hz), 2.94 (1H, d, J=4.1 Hz), 3.16 (1H, dd, J=7.8 Hz, J=5.6 Hz), 3.50 (3H, s), 3.75 (1H, dd, J=11.6 Hz, J=2.3 Hz), 5.22 (1H, m), 5.99 (1H, d, J=2.3 Hz), 7.45-7.65 (3H, m), 7.8-7.9 (1H, m).

EXAMPLE 7

O-Nicatinoylfumagillol

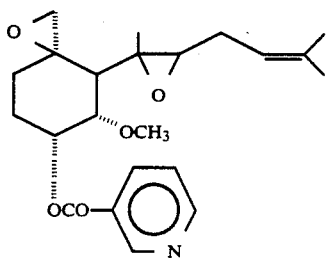

To a solution of fumagillol (500 mg) and dimethylaminopyridine (870 mg) in anhydrous dichloromethane (15 ml) was added nicotinoyl chloride hydrochloride (470 mg) and the mixture was stirred at room temperature for 30 minutes. The reaction mixture was diluted with ethyl acetate, washed with water, saturated aqueous sodium hydrogen carbonate solution and saturated aqueous sodium chloride solution and dried over anhydrous magnesium sulfate. The solvent was distilled off under reduced pressure and the residue was subjected to silica gel column chromatography. The ethyl acetate eluate was concentrated under reduced pressure to give colorless, oily O-nicotinoylfumagillol (629 mg) (92% yield).

¹H-NMR (CDCl₃) δ: 1.20 (1H, m), 1.24 (3H, s), 1.67 (3H, s), 1.76 (3H, s), 2.04 (1H, d, J=11.0 Hz), 1.95-2.47 (5H, m), 2.61 (1H, d, J=4.2 Hz), 2.63 (1H, t, J=6.4 Hz), 3.05 (1H, d, J=4.2 Hz), 3.50 (3H, s), 3.77 (1H, dd, J=11.0 Hz, J=2.8 Hz), 5.22 (1H, m), 5.95 (1H, m), 7.39 (1H, ddd, J=7.9 Hz, J=4.9 Hz, J=1.0 Hz), 8.29 (1H, dt, J=7.9 Hz, J=2.0 Hz), 8.78 (1H, dd, J=4.9 Hz, J=2.0 Hz), 9.22 (1H, dd, J=1.0 Hz, J=2.0 Hz).

EXAMPLE 8

O-Chloroacetylcarbamoylfumagillol

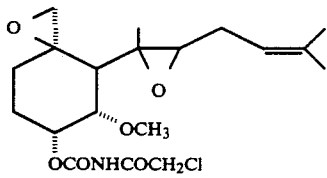

To a solution of fumagillol (314 mg) in dichloromethane (5 ml) was added dropwise chloroacetyl isocyanate (160 mg) under ice cooling, followed by addition of dimethylaminopyridine (130 mg). The mixture was stirred at 0° C. for 2 hours. To this reaction mixture was added water and the mixture was extracted with dichloromethane. The organic layer was washed with saturated aqueous sodium chloride solution and dried over anhydrous magnesium sulfate. The solvent was distilled off under reduced pressure and the residue was subjected to silica gel column chromatography. The eluate obtained with a mixture of n-hexane and ethyl acetate (3:1) was concentrated under reduced pressure to give colorless, powdery O-chloroacetylcarbamoylfumagillol (318 mg) (71% yield).

¹H-NMR (CDCl₃) δ: 1.10 (1H, m), 1.21 (3H, s), 1.66 (3H, s), 1.75 (3H, s), 1.93 (1H, d, J=11.4 Hz), 1.8-2.5 (5H, m), 2.57 (1H, d, J=4.2 Hz), 2.58 (1H, m) 2.99 (1H, d, J=4.2 Hz), 3.47 (3H, s), 3.68 (1H, dd, J=11.4 Hz, J=2.8 Hz), 4.44 (2H, s), 5.20 (1H, m), 5.61 (1H, m), 8.33 (1H, br s).

EXAMPLE 9

O-(n-Propylcarbamoyl)fumagillol

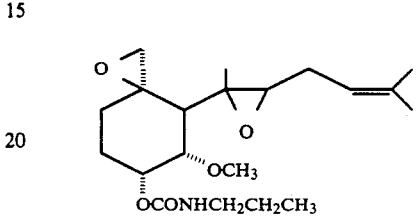

In the same manner as in Example 8, fumagillol (200 mg) was reacted with n-propyl isocyanate (180 mg) with stirring at room temperature for 3 days. Purification by silica gel column chromatography (n-hexane:ethyl acetate=4:1) gave colorless, powdery O-(n-propylcarbamoyl)fumagillol (128 mg) (49% yield).

¹H-NMR (CDCl₃) δ: 0.92 (3H, t, J=7.4 Hz), 1.07 (1H, m), 1.21 (3H, s), 1.4-2.5 (8H, m), 1.66 (3H, 1.75 (3H, 5), 2.55 (1H, d, J=4.2 Hz), 2.57 (1H, t, J=6.4 Hz), 2.98 (1H, d, J=4.2 Hz), 3.13 (2H, q, J=6.8 Hz), 3.45 (3H, s), 3.64 (1H, dd, J=11.2 Hz, J=2.8 Hz), 4.79 (1H, m), 5.21 (1H, m), 5.48 (1H, br s).

EXAMPLE 10

Sodium salt of O-carboxymethylcarbamoylfumagillol

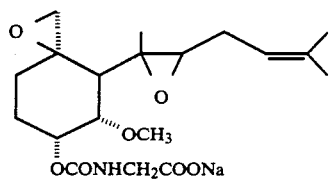

In the same manner as in Example 8, fumagillol (242 mg) was reacted with ethyl isocyanatoacetate (135 mg) with stirring at room temperature for 24 hours. Purification by silica gel column chromatography (n-hexane:ethyl acetate=3:1) gave colorless, oily O-ethoxycarbonylmethylcarbamoylfumagillol.

¹H-NMR (CDCl₃) δ: 1.08 (1H, m), 1.21 (3H, s), 1.29 (3E, t, J=7.2 Hz), 1.65 (3H, s), 1.74 (3H, s), 1.5-2.5 (6H, m), 2.55 (1H, d, J=4.2 Hz), 2.58 (1H, t, J=6.7 Hz), 2.98 (1H, d, J=4.2 Hz), 3.45 (3H, s), 3.63 (1H, dd, J=11.2 Hz, J=2.6 Hz), 3.87 (1H, dd, J=18.6 Hz, J=4.8 Hz), 4.06 (1H, dd, J=18.6 Hz, J=6.0 Hz), 4.22 (2H, q, J=7.2 Hz), 5.15-5.35 (2H, m), 6.00 (1H, m).

To a solution of O-ethoxycarbonylmethylcarbamoylfumagillol in ethanol (3 ml) was added 1N sodium hydroxide (2 ml) and the mixture was stirred at room temperature for 2 hours. The reaction mixture was concentrated under reduced pressure, water was added to the residue and the mixture was washed with ethyl acetate. The aqueous layer was adjusted to pH 3 with oxalic acid and extracted with ethyl acetate. The extract was dried over anhydrous magnesium sulfate. Then the solvent was distilled off under reduced pressure to give light yellow, powdery O-carboxymethylcarbamoylfumagillol (251 mg) (76% yield).

¹H- (CDCl₃) 1.07 (1H, m), 1.22 (3H, s), 1.64 (3H, s), 1.75 (3H, s), 1.5–2.5 (6H, m), 2.56 (1H, d, J=4.2 Hz), 2.68 (1H, m), 2.97 (1H, d, J=4.2 Hz), 3.44 (3H, s), 3.68 (1H, dd, J=11.2 Hz, J=2.6 Hz), 3.99 (2H, m), 5.19 (1H, m), 5.47 (1H, m), 5.62 (1H, m)

To O-carboxymethylcarbamoylfumagillol (130 mg) was added water (1 ml), followed by portionwise addition of sodium hydrogen carbonate (40 mg) for dissolving the starting material. The solvent was distilled off under reduced pressure to give colorless, powdery sodium salt of O-carboxymethylcarbamoylfumagillol (135 mg) (98% yield).

m.p.: gradual decomposition above 200° C.

¹H-NMR (D₂O) δ: 1.10 (1H, m), 1.23 (3H, s), 1.68 (3H, s), 1.77 (3H, s), 1.5–2.5 (6H, m), 2.78 (1H, d, J=3.2 Hz), 2.90 (1H, m), 3.12 (1H, d, J=3.2 Hz), 3.45 (3H, s), 3.70 (2H, s), 3.84 (1H, dd, J=11.5 Hz, J=2.6 Hz), 5.29 (1H, m), 5.49 (1H, m).

EXAMPLE 11

O-Phenylcarbamoylfumagillol

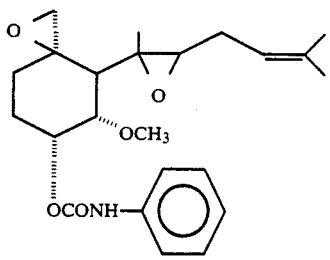

In the same manner as in Example 8, fumagillol (568 mg) was reacted with phenyl isocyanate (600 mg) with stirring at room temperature for 10 hours. Purification by silica gel column chromatography (n-hexane:ethyl acetate=4:1) gave colorless, powdery O-phenylcarbamoylfumagillol (310 mg) (39% yield).

¹H-NMR (CDCl₃) δ: 1.10 (1H, m), 1.23 (3H, s), 1.66 (3H, s), 1.75 (3H, s), 1.6–2.4 (6H, M), 2.56 (1H, d, J=4.2 Hz), 2.58 (1H, t, J=6.0 Hz), 3.00 (1H, d, J=4.2 Hz), 3.43 (3H, s), 3.70 (1H, dd, J=11.2 Hz, J=2.8 Hz), 5.21 (1H, m), 5.57 (1H, br s), 7.0–7.6 (6H, m).

EXAMPLE 12

O-(m-Trifluoromethylphenylcarbamoyl)fumagillol

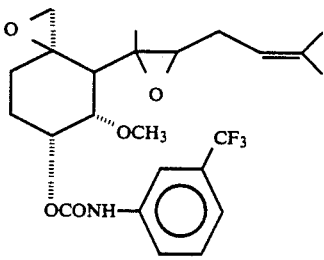

In the same manner as in Example 8, fumagillol (208 mg) was reacted with m-trifluoromethylphenyl isocyanate (207 mg) with stirring at room temperature for 15 hours. Purification by silica gel column chromatography (n-hexane: ethyl acetate=4:1) gave colorless, powdery O-(m-trifluoromethylphenylcarbamoyl)fumagillol (285 mg) (82% yield).

¹H-NMR (CDCl₃) δ: 1.12 (1H, m), 1.23 (3H, s), 1.67 (3H, s), 1.75 (3H, s), 1.99 (1H, d, J=11.2 Hz), 1.8–2.5 (5H, m), 2.59 (2H, m), 3.00 (1H, d, J=4.2 Hz), 3.48 (3H, s), 3.71 (1H, dd, J=11.2 Hz, J=2.7 Hz), 5.21 (1H, m), 5.60 (1H, m), 7.00 (1H, br s), 7.25–7.60 (3H, m), 7.76 (1H, br s).

EXAMPLE 13

O-(1-Naphtylcarbamoyl)fumagillol and O-(N-(1-naphtylcarbamoyl)-N-(1-naphtyl)carbamoyl]-fumagillol

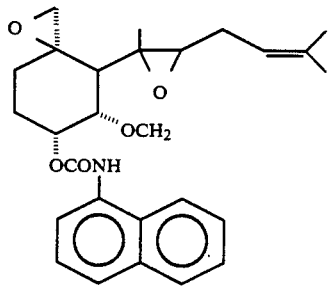

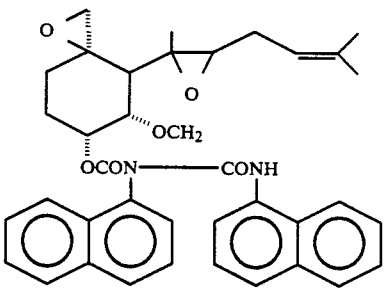

In the same manner as in Example 8, fumagillol (220 mg) was reacted with 1-naphtyl isocyanate (135 mg) with stirring at room temperature for 15 hours. Purification by silica gel column chromatography (n-hexane:ethyl acetate=9:1) gave colorless, powdery O-(N-(1-naphtyl carbamoyl)-N-(1-naphtyl)carbamoyl)-fumagillol (215 mg) (44% yield).

1H-NMR (CDCl₁) δ: 0.50 (1H, m), 0.90 (1H, m), 0.97 (3H×-2/5, s), 1.07 (3H×3/5, s), 1.30 (1H, m), 1.67 (3H, s), 1.77 (3H, s), 1.45–1.80 (2H, M), 1.9–2.4 (4H, m), 2.56 (1H×2/5, d, J=4.2 Hz), 2.69 (1H×3/5, d, J=4.2 Hz), 3.35–3.55 (1H, m), 3.50 (3H×2/5, s), 3.52 (3H×2/5, s), 5.20 (1H, m), 5.65 (1H, br s), 7.4–8.3 (14H, m), 11.65 (1H, br s).

The subsequent elution from the silica gel column with n-hexane-ethyl acetate (4:1) gave colorless, powdery O-(1-naphtylcarbamoyl)fumagillol (161 mg) (46% yield).

¹H-NMR (CDCl₃) δ: 1.10 (1H, m), 1.24 (3H, s), 1.67 (3H, s), 1.75 (3H, s), 1.6–2.5 (6H, m), 2.55 (1H, d, J=4.2 Hz), 2.59 (1H, m), 2.99 (1H, d, J=4.2 Hz), 3.47 (3H, s), 3.70 (1H, dd, J=11.2 Hz, J=2.6 Hz), 5.22 (1H, m), 5.63 (1H, br s), 7.19 (1H, br s), 7.4–8.0 (7H, m).

EXAMPLE 14

O-Methylfumagillol

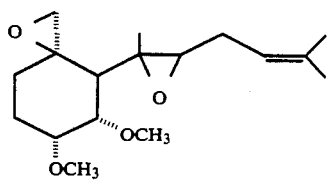

To a solution of fumagillol (233 mg) in anhydrous THF (1.5 ml) and anhydrous DMF (1.5 ml) was added 60% sodium hydride (70 mg) under ice cooling, followed by slow dropwise addition of methyl iodide (230 mg) and, after completion of the dropping, the mixture was stirred at 0° C. for 20 minutes. To the reaction mixture was added water and the mixture was extracted with ether. The organic layer was washed with saturated aqueous sodium chloride solution and dried over anhydrous magnesium sulfate. The solvent was distilled off under reduced pressure and the residue was subjected to silica gel colum chromatography. The eluate obtained with a mixture of n-hexane and ethyl acetate (2:1) was concentrated under reduced pressure to give colorless, oily O-methylfumagillol (281 mg) (95% yield).

$^1$H-NMR (CDCl$_3$) δ: 1.00 (1H, m), 1.21 (3H, s), 1.65 (3H, s), 1.74 (3H, s), 1.5–1.8 (1H, m), 2.04.(1H, d, J=11.2 Hz), 1.93–2.25 (3H, m), 2.3–2.5 (1H, m) 2.52 (1H, d, J=4.4 Hz), 2.55 (1H, t, J=5.8 Hz), 2.96 (1H, d, J=4.4 Hz), 3.44 (3H, s), 3.47 (3H, s), 3.59 (1H, dd, J=11.2 Hz, J=2.6 Hz), 3.93 (1H, m), 5.21 (1H, m).

EXAMPLE 15

O-Octadecylfumagillol

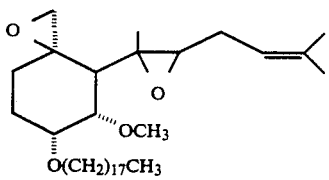

In the same manner as in Example 14, fumagillol (100 mg) was reacted with octadecyl iodide (160 mg) with stirring at room temperature for 2 days. Purification by silica gel column chromatography (dichloromethane) gave crystals, which were recrystallized from methanol-water to give colorless, crystalline O-octadecyl-fumagillol (85 mg) (45% yield).

m.p.: 58°–59° C.

$^1$H-NMR (CDCl$_3$) δ: 0.88 (3H, t, J=6.5 Hz), 1.00 (1H, m), 1.21 (3H, s), 1.25 (30H, s), 1.5–1.7 (3H, m), 1.63 (3H, s) 1.73 (3H, s), 1.9–2.4 (5H, m), 2.49 (1H, d, J=4.2 Hz), 2.56 (1H, t, J=5.8 Hz), 2.94 (1H, d, J=4.2 Hz), 3.45 (3H, s), 3.4–3.6 (3H, m), 3.98 (1H, m), 5.21 (1H, m).

EXAMPLE 16

O-Carboxymethylfumagillol

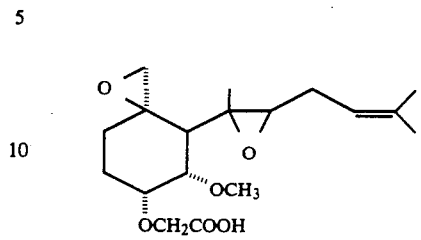

In the same manner as in Example 14, fumagillol (211 mg) was reacted with bromoacetic acid (135 mg) at room temperature for 2 hours. To the reaction mixture was added water and the mixture was washed with ether. The aqueous layer was adjusted to pH 4 with diluted hydrochloric acid and extracted with ether. The extract was dried over anhydrous magnesium sulfate and the solvent was distilled off under reduced pressure to give colorless, oily O-carboxymethylfumagillol (191 mg) (75% yield).

$^1$H-NMR (CDCl$_3$) δ: 1.03 (1H, m), 1.24 (3H, s), 1.66 (3H, s), 1.76 (3H, s), 1.7–2.4 (6H, m), 2.57 (1H, d, J=4.2 Hz), 2.60 (1H, t, J=5.8 Hz), 2.95 (1H, d, J=4.2 Hz), 3.58 (3H, s), 3.70 (1H, dd, J=11.2 Hz, J=2.6 Hz), 3.97 (1H, br 5), 4.05 (1H, d, J=17.5 Hz), 4.30 (1H, d, J=17.5 Hz), 5.20 (1H, m).

EXAMPLE 17

O-Benzylfumagillol

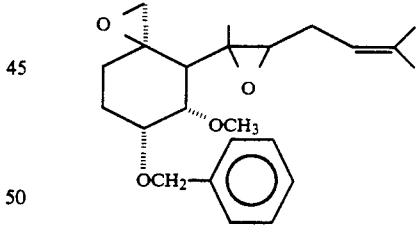

In the same manner as in Example 14, fumagillol (119 mg) was reacted with benzyl bromide (110 mg) at 0° C. for 30 minutes. Purification by silica gel column chromatography (n-hexane:ethyl acetate=5:1) gave colorless, oily O-benzylfumagillol (151 mg) (96% yield).

$^1$H-NMR (CDCl$_3$) δ: 1.02 (1H, m), 1.22 (3H, s), 1.68 (3H, s), 1.69 (1H, M)t 1.75 (3H, s), 2.00 (1H, M), 2.1–2.25 (3H, m), 2.45 (1H, m), 2.50 (1H, d, J=4.2 Hz), 2.57 (1H, t, J=5.8 Hz), 2.98 (1H, d, J=4.2 Hz), 3.41 (3H, s), 3.59 (1H, dd, J=11.2 Hz, J=2.6 Hz)t 4.10 (1H, br s), 4.72 (2H, ABq, J=13 Hz), 5.23 (1H, m), 7.2–7.45 (5H, m).

EXAMPLE 18

O-(p-Bromobenzyl)fumagillol

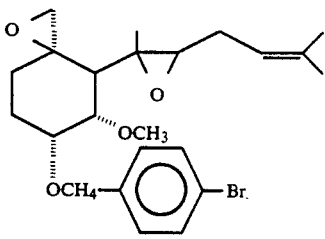

In the same manner as in Example 14, fumagillol (100 mg) was reacted with p-bromobenzyl bromide (354 mg) at 0° C. for 1 hour. Purification by silica gel column chromatography (n-hexane:ethyl acetate=5:1) gave colorless, oily O-(p-bromobenzyl)fumagillol (135 mg) (84% yield).

$^1$H-NMR (CDCl$_3$) δ: 1.01 (1H, m), 1.21 (3H, s), 1.65 (3H, s), 1.74 (3H, s), 1.55-1.7 (1H, m), 1.9-2.5 (4H, m), 2.12 (1H, d, J=11.0 Hz), 2.52 (1H, d, J=4.4 Hz), 2.57 (1H, t, J=6.2 Hz), 2.96 (1H, d, J=4.4 Hz), 3.41 (3H, s), 3.58 (1H, dd, J=11.0 Hz, J=2.4 Hz), 4.09 (1H, m), 4.65 (2H, ABq, J=12.8 Hz), 5.21 (1H, m), 7.27 (2H, d, J=8.6 Hz), 7.45 (2H, d, J=8.6 Hz).

EXAMPLE 19

O-(2,3-Epoxypropyl)fumagillol

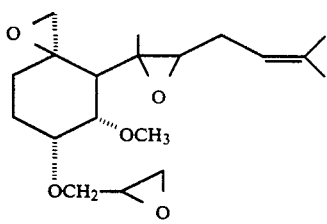

In the same manner as in Example 14, fumagillol (215 mg) was reacted with epibromohydrin (125 mg) at room temperature for 5 hours. Purification by silica gel column chromatography (n-hexane:ethyl acetate=2:1) gave colorless, oily O-(2,3-epoxypropyl)fumagillol (225 mg) (87% yield).

$^1$H-NMR (CDCl$_3$) δ: 0.98 (1H, m), 1.22 (3H, s), 1.63 (3H×½, s), 1.65 (3H×½, s), 1.75 (3H, s), 1.6-1.7 (1H, m), 1.9-2.4 (5H, m), 2.5-2.65 (3H, m), 2.77 (1H, m), 2.96 (1H, d, J=4.2 Hz), 3.17 (1H, m), 3.47 (3H×½, s), 3.50 (3H×½, s), 3.35-4.05 (2H, m), 4.02 (1H×½, br s), 4.07 (1H×½, br s), 5.21 (1H, m).

EXAMPLE 20

O-(p-Toluenesulfonyl)fumagillol

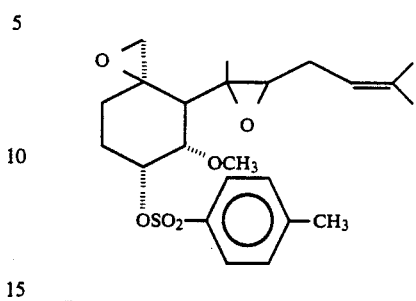

To a solution of fumagillol (3.00 g) and dimethylaminopyridine (3.24 g) in anhydrous dichloromethane (30 ml) was added p-toluenesulfonyl chloride (3.04 g) and the mixture was stirred overnight at room temperature. The reaction mixture was diluted with dichloromethane, washed with saturated aqueous sodium chloride solution and dried over anhydrous magnesium sulfate. The solvent was distilled off under reduced pressure and the residue was subjected to silica gel column chromatography using n-hexane-ethyl acetate (4:1) as an eluent. The eluate was concentrated under reduced pressure and the resulting crude crystals were recrystallized from diisopropyl ether to give colorless, crystalline O-(p-toluenesulfonyl)fumagillol (2.88 g).

m.p.: 123°-124° C.

$^1$H-NMR (CDCl$_3$) δ: 1.14 (1H, m), 1.16 (3H, s), 1.67 (3H, s), 1.70 (3H, s), 1.84 (1H, m), 1.95 (1H, d, J=10.7 Hz), 2.04-2.47 (4H, m), 2.44 (3H, s), 2.55 (1H, d, J=4.3 Hz), 2.56 (1H, t, J=6.4 Hz), 2.94 (1H, d, J=4.3 Hz), 3.02 (3H, s), 3.50 (1H, dd, J=10.7 Hz, J=2.5 Hz), 5.07 (1H, M), 5.19 (1H, m), 7.33 (2H, d, J=8.2 Hz), 7.87 (2H, d, J=8.2 Hz).

EXAMPLE 21

O-Methylsulfonylfumagillol

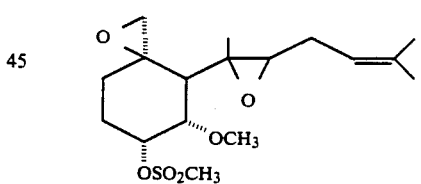

To a solution of fumagillol (500 mg) and dimethylaminopyridine (541 mg) in anhydrous dichloromethane (5 ml) was added dropwise methanesulfonyl chloride (0.21 ml) under ice cooling and the mixture was stirred at room temperature for 1 hour. The reaction mixture was diluted with ethyl acetate, washed with water and saturated aqueous sodium chloride solution and dried over anhydrous magnesium sulfate. The solvent was distilled off under reduced pressure and the residue was subjected to silica gel column chromatography using n-hexane-ethyl acetate (2:1) as an eluent. The eluate was concentrated under reduced pressure to give O-methylsulfonylfumagillol as a colorless oil (561 mg).

$^1$H-NMR (CDCl$_3$) δ: 1.12 (1H, m), 1.20 (3H, s), 1.66 (3H, s), 1.75 (3H, s), 1.93 (1H, d, J=11.4 Hz), 1.85-2.45 (4H, m), 2.58 (1H, t, J=6.4 Hz), 2.59 (1H, d, J=4.2 Hz), 2.99 (1H, d, J=4.2 Hz), 3.14 (3H, s), 3.53 (3H, s), 3.65

(1H, dd, J=2.4 Hz, J=11.4 Hz), 5.20 (1H, m), 5.39 (1H, m).

EXAMPLE 22

O-Phenoxycarbonylfumagillol

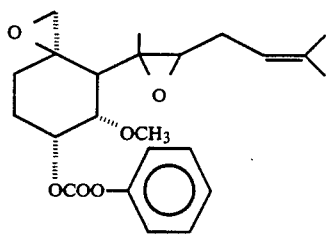

Fumagillol (133 mg) and dimethylaminopyridine (115 mg) were dissolved in dichloromethane (3 ml), followed by addition of phenyl chloroformate (111 mg). The mixture was stirred at room temperature for 30 minutes. After addition of water, the mixture was diluted with dichloromethane (30 ml), washed with water and saturated aqueous sodium chloride solution and dried over anhydrous magnesium sulfate. The solvent was distilled off under reduced pressure and the residue was subjected to silica gel column chromatography (eluent: n-hexane-ethyl acetate=5:1) to give colorless, oily O-phenoxycarbonylfumagillol (174 mg) (92% yield).

$^1$H-NMR (CDCl$_3$) δ: 1.10 (1H, m), 1.22 (3H, s), 1.66 (3H, s), 1.75 (3H, s), 1.8-2.45 (6H, m), 2.56 (1H, d, J=4.4 Hz), 2.59 (1H, t, J=6.4 Hz), 2.99 (1H, d, J=4.4 Hz), 3.50 (3H, s), 3.69 (1H, dd, J=11.2 Hz, J=2.6 Hz), 5.18 (1H, m), 5.58 (1H, br s), 7.15-7.45 (5H,

EXAMPLE 23

O-Carbamoylfumagillol

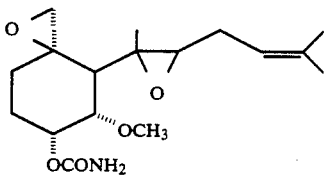

O-Phenoxycarbonylfumagillol (402 mg) was dissolved in ethanol (5 ml), followed by addition of concentrated aqueous ammonia (3 ml). The mixture was sitrred at room temperature for 3 hours. The solvent was distilled off under reduced pressure and the residue was subjected to silica gel column chromatography (eluent: n-hexane-ethyl acetate=1:1) to give colorless, powdery O-carbamoylfumagillol (273 mg) (84% yield).
m.p.: 125°-126° C.

$^1$H-NMR (CDCl$_3$) δ: 1.07 (1H, m), 1.21 (3H, s), 1.66 (3H, s), 1.75 (3H, s), 1.6-2.5 (6H, m), 2.55 (1H, d-, J=4.4 Hz), 2.57 (1H, t, J=7.4 Hz), 2.98 (1H, d, J=4 .4 Hz), 3.45 (3H, s), 3.65 (1H, dd, J=11.4 Hz, J=2.8 Hz), 5.09 (2H, br s), 5.21 (1H, br t, J=7.6 Hz), 5.46 (1H, br s).

EXAMPLE 24

O-Morpholinocarbonylfumagillol

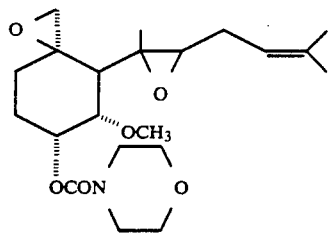

In the same manner as in Example 23, O-phenoxycarbonylfumagillol (173 mg) was reacted with morpholine (200 mg) with stirring at room temperature for 20 hours. Purification by silica gel column chromatography (eluent: n-hexane-ethyl acetate=1:1) gave colorless, oily O-morpholinocarbonylfumagillol (148 mg) (87% yield).

$^1$H-NMR (CDCl$_3$) δ: 1.11 (1H, m), 1.21 (3H, s), 1.66 (3H, s), 1.74 (3H, s), 1.6-2.5 (6H, m), 2.55 (1H, d, J=4.2 Hz), 2.57 (1H, t, J=5.6 Hz), 2.99 (1H, d, J=4.2 Hz), 3.46 (3H, s), 3.47 (4H, m), 3.68 (5H, m), 5.21 (1H, m), 5.57 (1H, br s).

EXAMPLE 25

O-Piperidinocarbonylfumagillol

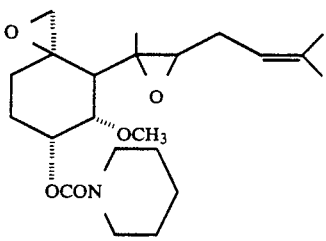

In the same manner as in Example 23, O-phenoxycarbonylfumagillol (193 mg) was reacted with piperidine (222 mg) with stirring at room tempertature for 6 hours. Purification by silica gel column chromatography (eluent: n-hexane-ethyl acetate=4:1) gave colorless, oily O-piperidinocarbonylfumagillol (187 mg) (99% yield).

$^1$H-NMR (CDCl$_3$) δ: 1.10 (1H, m), 1.22 (3H, s), 1.57 (6H, m), 1.66 (3H, s), 1.74 (3H, s), 1.8-2.5 (6H, m), 2.55 (1H, d, J=4.2 Hz), 2.59 (1H, t, J=6.4 Hz), 2.99 (1H, d, J=4.2 Hz), 3.42 (4H, m), 3.46 (3H, s)., 3.64 (1H, dd, J=11.0 Hz, J=2.8 Hz), 5.22 (1H, m), 5.56 (1H, br s),

EXAMPLE 26

O-Carbazoylfumagillol

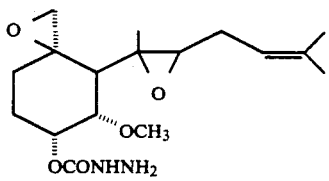

In the same manner as in Example 23, O-phenoxycarbonylfumagillol (400 mg) was reacted with hydrazine (120 mg) with stirring at room temperature for 1 hour. Purifcation by silica gel column chromatography (eluent: n-hexane-ethyl acetate=1:2) gave light yellow, powdery O-carbazoylfumagillol (169 mg) (50% yield).

¹H-NMR (CDCl₃) δ: 1.07 (1H, m), 1.21 (3H, s), 1.65 (3H, s), 1.74 (3H, s), 1.6–2.5 (6H, m), 2.55 (1H, d, J=4.2 Hz), 2.56 (1H, t, J=6.4 Hz), 2.98 (1H, d, J=4.2 Hz), 3.47 (3H, s), 3.65 (1H, dd, J=11.2 Hz, J=2.8 Hz), 3.70 (2H, br s), 5.20 (1H, m), 5.55 (1H, m), 6.19 (1H, br s).

EXAMPLE 27

O-(1-Imidazolylcarbonyl)fumagillol

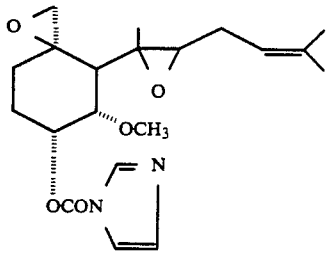

To a solution of fumagillol (236 mg) in dichloromethane (5 ml) was added 1,1'-carbonyldiimidazole (410 mg) and the mixture was stirred at room temperature for 1 day. The reaction mixture was concentrated under reduced pressure and the residue was subjected to silica gel column chromatography (eluent: n-hexane-ethyl acetate=3:2) to give colorless, oily O-(1-imidazolylcarbonyl)fumagillol (275 mg) (90% yield).

¹H-NMR (CDCl₃) δ: 1.20 (1H, m), 1.23 (3H, s), 1.67 (3H, s), 1.75 (3H, s), 1.91 (1H, d, J=11.2 Hz), 1.8–2.5 (5H, m), 2.62 (1H, t, J=6.4 Hz), 2.62 (1H, d, J=4.2 Hz), 3.04 (1H, d, J=4.2 Hz), 3.52 (3H, s), 3.77 (1H, dd, J=11.2 Hz, J=2.6 Hz), 5.21 (1H, m), 5.83 (1H, br s), 7.06 (1H, d, J=1.4 Hz), 7.41 (1H, t, J=1.4 Hz), 8.12 (1H, s).

EXAMPLE 28

O-(2-dimethylaminoethylcarbamoyl)fumagillol

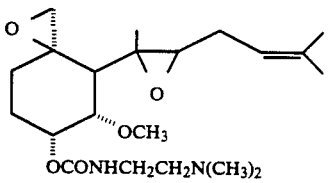

To a solution of O-(1-imidazolylcarbonyl)fumagillol (270 mg) in dichloromethane (3 ml) was added 2-dimethylaminoethylamine (90 mg) and the mixture was sitrred at room temperature for 1 day. The reaction mixture was diluted with ethyl acetate, washed with saturated aqueous sodium hydrogen carbonate solution, water and saturated aqueous sodium chloride solution and dried over anhydrous magesium sulfate. The solvent was distilled off under reduced pressure and the residue was subjected to silica gel column chromatography (eluent: chloroform-methanol=20:1) to give colorless, powdery O-(2-dimethylaminoethylcarbamoyl)fumagillol (139 mg) (53% yield).

¹H-NMR (CDCl₃) δ: 1.08 (1H, m), 1.22 (3H, s), 1.66 (3H, s), 1.75 (3H, s), 2.23 (6H, m), 1.6–2.5 (6H, m), 2.41 (2H, t, J=6.0 Hz), 2.55 (1H, d, J=4.4 Hz), 2.58 (1H, t, J=6.6 Hz), 2.98 (1H, d, J=4.4 Hz), 3.23 (2H, m), 3.46 (3H, s), 3.65 (1H, dd, J=11.2 Hz, J=2.8 Hz), 5.21 (1H, m), 5.39 (1H, br t), 5.50 (1H, br s).

EXAMPLE 29

O-Acetylcarbamoylfumagillol

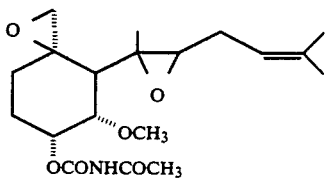

In the same manner as in Example 8, fumagillol (700 mg) was reacted with acetyl isocyanate (500 mg) with stirring at room temperature for 10 minutes. Purification by silica gel column chromatography (eluent: n-hexane-ethyl acetate=2:1) gave colorless, syrupy O-acetylcarbamoylfumagillol (825 mg) (91% yield).

¹H-NMR (CDCl₃) δ: 1.10 (1H, m), 1.21 (3H, s), 1.66 (3H. s), 1.75 (3H, S), 1.8–2.5 (6H, m), 2.39 (3H, s), 2.57 (1H, t, J=6.8 Hz), 2.58 (1H, d, J=4.2 Hz), 2.99 (1H, d, J=4.2 Hz), 3.47 (3H, s), 3.68 (1H, dd, J=11.4 Hz, J=2.8 Hz), 5.20 (1H, m), 5.57 (1H, br s), 8.03 (1H, br s).

EXAMPLE 30

O-Dichloroacetylcarbamoylfumagillol

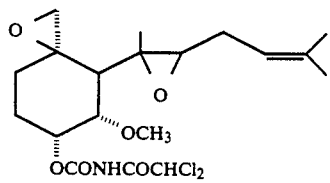

In the same manner as in Example 8, fumagillol (570 mg) was reacted with dichloroacetyl isocyanate (500 mg) with stirring at room temperature for 10 minutes. Purification by silica gel column chromatography (eluent: n-hexane-ethyl acetate=3:1) gave colorless, syrupy O-dichloroacetylcarbamoylfumagillol (789 mg) (90% yield).

¹H-NMR (CDCl₃) δ: 1.11 (1H, m), 1.22 (3H, s), 1.67 (3H, s), 1.75 (3H, s), 1.96 (1H, d, J=11.2 Hz), 1.6–2.6 (6H, m), 2.58 (1H, d, J=4.2 Hz), 2.99 (1H, d, J=4.2 Hz), 3.48 (3H, s), 3.71 (1H, dd, J=11.2 Hz, J=2.8 Hz), 5.20 (1H, m), 5.64 (1H, m), 6.38 (1H, s), 8.50 (1H, s).

EXAMPLE 31

O-Trichloroacetylcarbamoylfumagillol

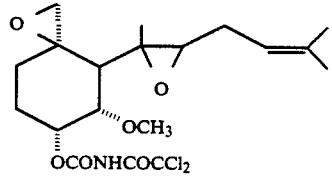

In the same manner as in Example 8, fumagillol (355 mg) was reacted with trichloroacetyl isocyanate (355 mg) with stirring at room temperature for 10 minutes. Purification by silica gel column chromatography (eluent: n-hexane-ethyl acetate=7:2) gave colorless, powdery O-trichloroacetylcarbamoylfumagillol (258 mg) (44% yield).

$^1$H-NMR (CDCl$_3$) δ: 1.11 (1H, m), 1.22 (3H, s), 1.66 (3H, s), 1.75 (3H, s), 2.00 (1H, d, J=11.4 Hz), 1.6–2.7 (6H, m), 2.58 (1H, d, J=4.2 Hz), 3.01 (1H, d, J=4.2 Hz), 3.50 (3H, s), 3.73 (1H, dd, J=11.4 Hz, J=2.8 Hz), 5.20 (1H, m), 5.71 (1H, m), 8.68 (1H, br s).

EXAMPLE 32

O-Benzoylcarbamoylfumagillol

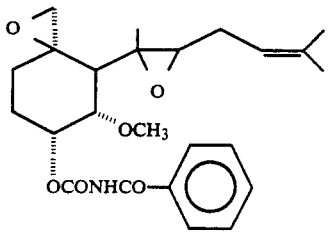

In the same manner as in Example 8, fumagillol (510 mg) was reacted with benzoyl isocyanate (530 mg) with stirring at room temperature for 30 minutes. Purification by silica gel column chromatography (eluent: n-hexane-ethyl acetate=3:1) gave colorless, powdery O-benzoylcarbamoylfumagillol (450 mg) (58% yield).

$^1$H-NMR (CDCl$_3$) δ: 1.09 (1H, m), 1.20 (3H, s), 1.65 (3H, s), 1.74 (3H, s), 1.6–2.45 (6H, m), 2.55 (1H, d, J=4.2 Hz), 2.56 (1H, t, J=7.0 Hz), 2.97 (1H, d, J=4.2 Hz), 3.42 (3H, s), 3.68 (1H, dd, J=11.4 Hz, J=2.6 Hz), 5.19 (1H, br t, J=7.4 Hz), 6.65 (1H, br s), 7.4–7.6 (3H, m), 7.89 (2H, dd, J=7.0 Hz, J=1.4 Hz), 8.88 (1H, br s).

EXAMPLE 33

O-Methacryloylcarbamoylfumagillol

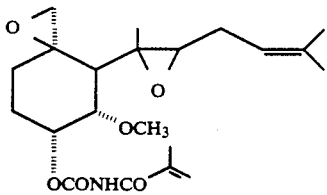

In the same manner as in Example 8, fumagillol (1 g) was reacted with methacryloyl isocyanate (900 mg) with stirring at room temperature for 10 minutes. Purification by silica gel column chromatography (eluent: n-hexane-ethyl acetate=2:1) gave colorless, powdery O-methacryloylcarbamoylfumagillol (511 mg) (37% yield).

m.p.: 480° C. $^1$H-NMR (CDCl$_3$) δ: 1.10 (1H, M), 1.22 (3H, s), 1.66 (3H, s), 1.76 (3H, s), 2.00 (3H, s), 1.6–2.5 (6H, m), 2.57 (1H, d, J=4.4 Hz), 2.60 (1H, t, J=6.0 Hz), 2.99 (1H, d, J=4.4 Hz), 3.47 (3H, s), 3.70 (1H, dd, J=11.4 Hz, J=2.8 Hz), 5.21 (1H, m), 5.58 (1H, d, J=1.6 Hz), 5.64 (1H, d, J=2.6 Hz), 5.79 (1H, s), 7.94 (1H, br s).

EXAMPLE 34

O-(2-Chloroethylcarbamoyl)fumagillol

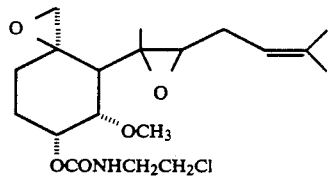

In the same manner as in Example 8, fumagillol (263 mg) was reacted with 2-chloroethyl isocyanate (150 mg) with stirring at room temperature for 1 day. Purification by silica gel column chromatography (eluent: n-hexane-ethyl acetate=3:1) gave colorless, powdery O-(2-chloroethylcarbamoyl)fumagillol (100 mg) (29% yield). $^1$H-NMR (CDCl$_3$) δ: 1.08 (1H, m), 1.21 (3H, s), 1.66 (3H, s), 1.75 (3H, s), 1.6–2.5 (6H, m), 2.56 (1H, d, J=4.4 Hz), 2.57 (1H, t, J=6.0 Hz), 2.98 (1H, d, J=4.4 Hz), 3.46 (3H, s), 3.4–3.7 (5H, m), 5.20 (2H, m), 5.50 (1H, br s).

EXAMPLE 35

O-(p-Chlorophenylcarbamoyl)fumagillol

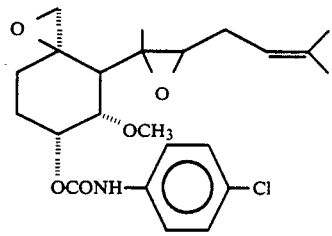

In the same manner as in Example 8, fumagillol (248 mg) was reacted with p-chlorophenyl isocyanate (200 mg) with stirring at room temperature for 1.5 hours. Purification by silica gel column chromatography (eluent: n-hexane-ethyl acetate=5:1) gave colorless, powdery O-(p-chlorophenylcarbamoyl)fumagillol (298 mg) (78% yield).

$^1$H-NMR (CDCl$_3$) δ: 1.09 (1H, m), 1.24 (3H, s), 1.66 (3H, s), 1.75 (3E, s), 1.6–2.5 (6H, m), 2.56 (1H, t, J=6.4 Hz), 2.57 (1H, d, J=4.2 Hz), 2.99 (1H, d, J=4.2 Hz), 3.40 (3H, s), 3.69 (1H, dd, J=11.2 Hz, J=2.6 Hz), 5.20 (1H, m), 5.57 (1H, br s), 7.24 (2H, d, J=9.0 Hz), 7.32 (1H, br s), 7.37 (2H, d, J=9.0 Hz).

EXAMPLE 36

O-(p-Nitrophenylcarbamoyl)fumagillol

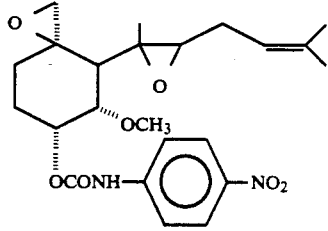

In the same manner as in Example 8, fumagillol (290 mg) was reacted with p-nitrophenyl isocyanate (500 mg) with stirring at room temperature for 20 hours. Purification by silica gel column chromatography (eluent: n-hexane-ethyl acetate=5:1) gave light yellow, powdery O-(p-nitrophenylcarbamoyl)fumagillol (255 mg) (56% yield).

$^1$H-NMR (CDCl$_3$) δ: 1.01 (1H, m), 1.29 (3H, s), 1.65 (3H, s), 1.75 (3H, s), 1.8-2.5 (6H, m), 2.58 (1H, t, J=6.2 Hz), 2.61 (1H, d, J=4.2 Hz), 3.01 (1H, d, J=4.2 Hz), 3.39 (3H, s), 3.75 (1H, dd, J=11.2 Hz, J=2.6 Hz), 5.20 (1H, m), 5.64 (1H, br s), 7.62 (2H, d, J=9.2 Hz), 8.15 (2H, d, J=9.2 Hz), 8.29 (1H, s).

EXAMPLE 37

O-(2,4-Difluorophenylcarbamoyl)fumagillol

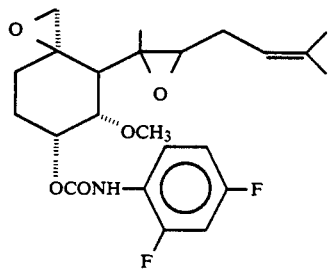

In the same manner as in Example 8, fumagillol (250 mg) was reacted with 2,4-difluorophenyl isocyanate (250 mg) with stirring at room temperature for 2 hours. Purification by silica gel column chromatography (eluent: n-hexane-ethyl acetate=4:1) gave colorless, powdery O-(2,4-difluorophenylcarbamoyl)fumagillol (246 mg) (63% yield).

$^1$H-NMR (CDCl$_3$) δ: 1.11 (1H, m, 1.23 (3H, s), 1.66 (3H, s), 1.75 (3H, s), 1.6-2.5 (6H, m), 2.58 (2H, m), 3.00 (1H, d, J=4.0 Hz), 3.49 (3H, s), 3.70 (1H, dd, J=11.4 Hz, J=2.8 Hz), 5.22 (1H, br t, J=7.4 Hz), 5.60 (1H, br s), 6.8-7.0 (3H, m), 8.05 (1H, br q, J=7.0 Hz).

EXAMPLE 38

O-(p-Toluenesulfonylcarbamoyl)fumagillol

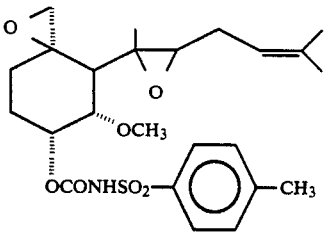

In the same manner as in Example 8, fumagillol (213 mg) was reacted with p-toluenesulfonyl isocyanate (250 mg) with stirring at room temperature for 2 hours. Purification by silica gel colum chromatogrpahy (eluent: n-hexane-ethyl acetate=2:1) gave colorless, powdery O-(p-toluenesulfonylcarbamoyl)fumagillol (247 mg) (68% yield).

$^1$H-NMR (CDCl$_3$) δ: 1.08 (1H, m), 1.18 (3H, s), 1.66 (3H, s), 1.75 (3H, s), 2.44 (3H, s), 1.6-2.6 (6H, m), 2.55 (1H, d, J=4.2 Hz), 2.57 (1H, t, J=6.3 Hz), 3.26 (3H, 5), 3.60 (1H, dd, J=11.2 Hz, J=2.6 Hz), 5.19 (1H, m), 5.42 (1H, br s), 7.34 (2H, d, J=8.0 Hz), 7.94 (2H, d, J=8.0 Hz), 8.60 (1H, br s).

EXAMPLE 39

O-[1-(4-Ethylpiperazinyl)carbonyl]fumagillol

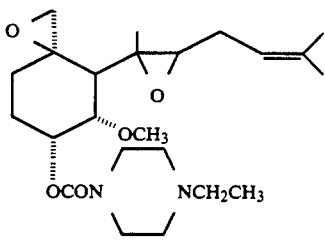

To a solution of fumagillol (235 mg) and dimethylaminopyridine (425 mg) in dichloromethane (3 ml) was added 1-(4-ethylpiperazinyl)carbonyl chloride (325 mg) and the mixture was stirred at room temperature for 3 hours. The reaction mixture was diluted with ethyl acetate, washed with water and saturated aqueous sodium chloride solution and dried over anhydrous magnesium sulfate. The solvent was distilled off under reduced pressure and the residue was purified by silica gel column chromatography (eluent: n-hexane-ethyl acetate=5:1) to give colorless, powdery O-[1-(4-ethylpiperazinyl)carbonyl]fumagillol (134 mg) (38% yield).

$^1$H-NMR (CDCl$_3$) δ: 1.05 (1H, m), 1.19 (3H, s), 1.22 (3H, t, J=7.2 Hz), 1.66 (3H, s), 1.75 (3E, s), 1.6-2.7 (12H, m), 2.24 (1H, d, J=4.2 Hz), 2.62 (1H, t, J=6.2 Hz), 2.98 (1H, d, J=4.2 Hz), 3.49 (3H, s), 3.69 (1H, dd, J=11.2 Hz, J=2.4 Hz), 3.4-4.2 (4H, m), 5.20 (1H, m), 5.70 (1H, br s).

EXAMPLE 40

O-Acetoxyacetylcarbamoylfumagillol

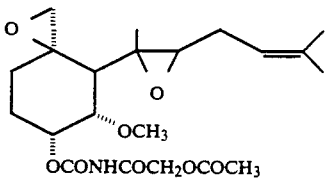

To a solution of O-chloroacetylcarbamoylfumagillol (201 mg) in dimethylformamide (3 ml) was added sodium acetate (200 mg) and the mixture was stirred at 60° C. for 1 hour. The reaction mixture was diluted with ethyl acetate, washed with water and saturated aqueous sodium chloride solution and dried over anhydrous magnesium sulfate. The solvent was distilled off under reduced pressure and the residue was purified by silica gel column chromatography (eluent: n-hexane-ethyl acetate=2:1) to give colorless, powdery O-acetoxyacetylcarbamoylfumagillol (165 mg) (77% yield).

$^1$H-NMR (CDCl$_3$) δ: 1.10 (1H, m), 1.21 (3H, s), 1.65 (3H, s), 1.74 (3H, s), 1.6-2.5 (6H, m), 2.18 (3H, s), 2.56 (2H, m), 2.99 (1H, d, J=4.0 Hz), 3.45 (3H, s), 3.67 (1H, dd, J=11.0 Hz, J=2.4 Hz), 4.96 (1H, d, J=17.4 Hz), 5.06 (1H, d, J=17.4 Hz), 5.19 (1H, br t, J=7.0 Hz), 5.56 (1H, br s), 8.55 (1H, s).

EXAMPLE 41

O-Acetylthioacetylcarbamoylfumagillol

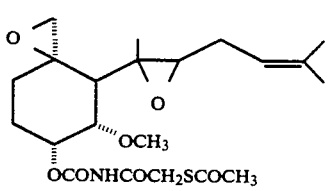

To a solution of O-chloroacetylcarbamoylfumagillol (155 mg) in dimethylformamide (2 ml) was added potassium thioacetate (70 mg) and the mixture was stirred at room temperature for 1 minute. The reaction mixture was diluted with ethyl acetate, washed with water and saturated aqueous sodium chloride solution and dried over anhydrous magnesium sulfate. The solvent was distilled off under reduced pressure and the residue was purified by silica gel column chromatography (eluent: n-hexane-ethyl acetate=2:1) to give colorless, powdery O-acetylthioacetylcarbamoylfumagillol (156 mg) (92% yield)

$^1$H-NMR (CDCl$_3$) δ: 1.10 (1H, m), 1.22 (3H, s), 1.67 (3H, s), 1.76 (3H, s), 1.8–2.5 (6H, m), 2.43 (3H, s), 2.43 (3E, s), 2.59 (1H, d, J=4.2 Hz), 2.60 (1H, t, J=6.7 Hz), 3.00 (1H, d, J=4.2 Hz), 3.48 (3H, s), 3.69 (1H, dd, J=11.2 Hz, J=2.6 Hz), 3.97 (1H, d, J=16.2 Hz), 4.07 (1H, d, J=16.2 Hz), 5.21 (1H, m), 5.63 (1H, m), 8.32 (1H, br s).

EXAMPLE 42

O-(2-Benzothiazolylthioacetylcarbamoyl)fumagillol

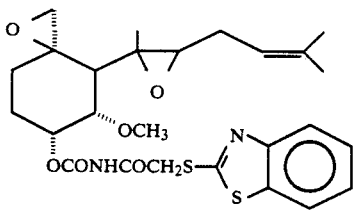

To a solution of O-chloroacetylcarbamoylfumagillol (160 mg) in dimethylformamide (2 ml) was added 2-mercaptobenzothiazole sodium (95 mg) and the mixture was stirred at room temperature for 1.5 hours. The reaction mixture was diluted with ethyl acetate, washed with water and saturated aqueous sodium chloride solution and dried over anhydrous magnesium sulfate. The solvent was distilled off under reduced pressure and the residue was purifed by silica gel column chromatography (eluent: n-hexane-ethyl acetate=3:1) to give colorless, powdery O-(2-benzothiazolylthioacetylcarbamoyl)fumagillol (152 mg) (72% yield).

$^1$H-NMR (CDCl$_3$) δ: 1.00 (1H, m), 1.20 (3H, s), 1.68 (3H, s), 1.78 (3H, s), 1.6–2.5 (7H, m), 2.51 (1H, d, J=4.2 Hz), 2.96 (1H, d, J=4.2 Hz), 3.48 (3H, s), 3.66 (1H, dd, J=11.4 Hz, J=2.8 Hz), 4.05 (1H, d, J=14.8 Hz), 4.24 (1H, d, J=14.8 Hz), 5.22 (1H, m), 5.65 (1H, br s), 7.3–7.5 (2H, m), 7.79 (1H, dd, J=7.2 Hz, J=1.4 Hz), 7.88 (1H, dd, J=7.2 Hz, J=1.4 Hz), 10.24 (1H, br s).

EXAMPLE 43

O-[(Pyridine-N-oxide-2-yl)thioacetylcarbamoyl]-fumagillol

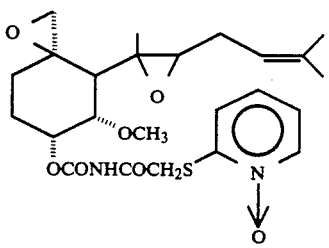

In the same manner as in Example 42, O-chloroacetylcarbamoylfumagillol (144 mg) was reacted with sodium pyridine-N-oxide-2-thiolate (60 mg) with stirring at room temperature for 10 minutes. Purification by silica gel column chromatography (eluent: chloroform-methanol=20:1) gave colorless, powdery O-C(pyridine-N-oxide-2-yl)thioacetylcarbamoyl]fumagillol (150 mg) (85% yield). $^1$H-NMR (CDCl$_3$) δ: 1.07 (1H, m), 1.21 (3H, s), 1.65 (3H, s), 1.74 (3H, s), 1.8–2.4 (EH, m), 2.55 (1H, d, J=4.4 Hz), 2.57 (1H, t, J=6.4 Hz), 2.98 (1H, d, J=4.4 Hz), 3.46 (3H, s), 3.68 (1H, dd, J=11.4 Hz, J=2.6 Hz), 3.94 (1H, d, J=15.4 Hz), 4.13 (1H, d, J=15.4 Hz), 5.19 (1H, m), 5.60 (1H, m), 7.1–7.35 (2H, m), 7.50 (1H, d, J=7.2 Hz), 8.33 (1H, d, J=6.2 Hz), 9.29 (1H, br s).

EXAMPLE 44

O-Diethylaminoacetylcarbamoylfumagillol

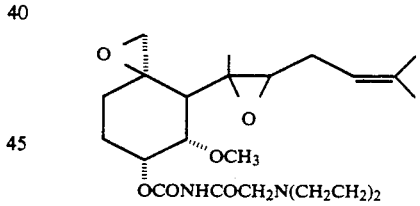

To a solution of O-chloroacetylcarbamoylfumagillol (154 mg) and triethylamine (35 mg) in toluene (2 ml) was added diethylamine (70 mg) and the mixture was stirred at room temperature for 1 day. The reaction mixture was diluted with ethyl acetate, washed with water and saturated aqueous sodium chloride solution and dried over anhydrous magnesium sulfate. The solvent was distilled off under reduced pressure and the residue was purified by silica gel column chromatography (eluent: n-hexane-ethyl acetate=2:1) to give colorless, syrupy O-diethylaminoacetylcarbamoylfumagillol (85 mg) (51% yeild).

$^1$H-NMR (CDCl$_3$) δ: 1.06 (6H, t, J=7.2 Hz), 1.10 (1H, m), 1.22 (3H, s), 1.66 (3H, s), 1.74 (3H, s), 1.5–2.7 (12H, m), 2.99 (2H, d, J=4.2 Hz), 3.15 (2H, t, J=7.5 Hz), 3.48 (3H, s), 3.68 (1H, dd, J=11.2 Hz, J=4.6 Hz), 5.20 (1H, m), 5.67 (1H, m), 55 (1H, br s).

EXAMPLE 45

O-Diphenylmethylfumagillol

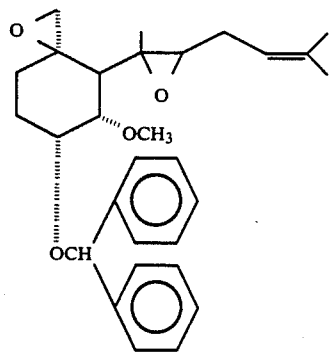

In the same manner as in Example 14, fumagillol (221 mg) was reacted with diphenylmethyl bromide (290 mg) with stirring at room temperature for 3 hours. Purification by silica gel column chromatography (eluent: n-hexane-ethyl acetate=10:1) gave colorless, oily O-diphenylmethylfumagillol (100 mg) (28% yield).

$^1$H-NMR (CDCl$_3$) δ: 0.98 (1H, m), 1.19 (3H, s), 1.58 (1H, m), 1.65 (3H, s), 1.73 (3H, s), 1.9–2.4 (5H, m), 2.49 (1H, d, J=4.2 Hz), 2.57 (1H, t, J=6.4 Hz), 2.96 (1H, d, J=4.2 Hz), 3.22 (3H, s), 3.51 (1H, dd, J=11.2 Hz, J=2.4 Hz), 4.12 (1H, br s), 5.21 (1H, m), 5w67 (1H, s), 7.1–7.5 (10H, m).

EXAMPLE 46

O-(1-Naphthylmethyl)fumagillol

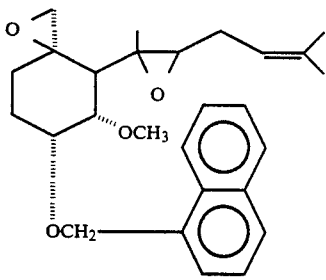

In the same manner as in Example 14, fumagillol (221 mg) was reacted with 1-chloromethylnaphthalene (215 mg) with stirring at room temperature for 2 hours. Purification by silica gel column chromatography (eluent: n-hexane-ethyl acetate=10:1) gave colorless, crystalline O-(1-naphtylmethyl)fumagillol (269 mg) (78% yield).

m.p.: 70–71° C. $^1$H-NMR (CDCl$_3$) δ: 0.95 (1H, m), 1.22 (3H, s), 1.65 (3H, s), 1.74 (3H, s), 1.5–2.5 (6H, m), 2.49 (1H, d, J=4.4 Hz), 2.57 (1H, t, J=6.4 Hz), 2.94 (1H, d, J=4.4 Hz), 3.42 (3H, s), 3.59 (1H, dd, J=11.0 Hz, J=2.4 Hz), 4.20 (1H, m), 5.03 (1H, d, J=11.4 Hz), 5.21 (1H, m), 5.28 (1H, d, J=11.4 Hz), 7.4–7.6 (4H, m), 7.8–7.9 (2H, m), 8.23 (1H, m).

EXAMPLE 47

O-(4-Picolyl)fumagillol

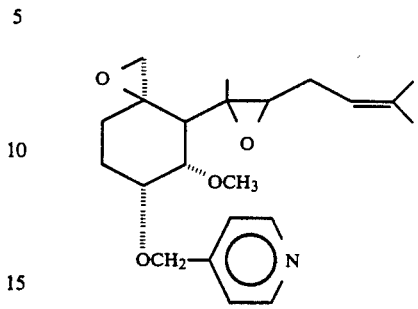

In the same manner as in Example 14, fumagillol (272 mg) was reacted with 4-picolyl chloride hydrochloride (240 mg) with stirring at room temperature for 2 hours. Purification by silica gel column chromatography (eluent: n-hexane-ethyl acetate=1:1) gave colorless, oily O-(4-picolyl)fumagillol (308 mg) (85% yield). $^1$H-NMR (CDCl$_3$) δ: 1.05 (1H, m), 1.22 (3H, s), 1.66 (3H, s), 1.74 (3H, s), 1.75 (1H, m), 1.95–2.45 (5H, m), 2.55 (1H, d, j=4.2 Hz), 2.59 (1H, t, J=6.4 Hz 2.98 (1H, d, J=4.2 Hz), 3.46 (3H, s), 3.63 (1H, dd, J=11.2 Hz, J=2.4 Hz), 4.14 (1H, m), 4.67 (1H, d, J=13.8 Hz), 4.81 (1H, d, J=13.8 Hz), 5.21 (1H, m), 7.31 (2H, d, J=5.8 Hz), 8.56 (2H, d, J=5.8 Hz).

EXAMPLE 48

O-(O-Bromomethylbenzyl)fumagillol

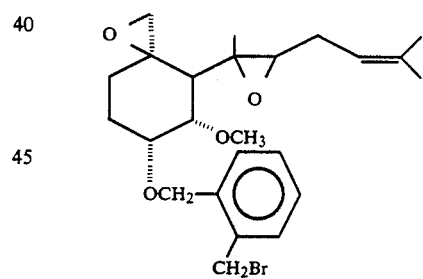

In the same manner as in Example 14, fumagillol (264 mg) was reacted with 1,2-dibromomethylbenzene (297 mg) with stirring at room temperature for 20 minutes. Purification by silica gel column chromatography (eluent: n-hexane-ethyl acetate=5:1) gave colorless, oily O-(O-bromomethylbenzyl)fumagillol (145 mg) (33% yield).

$^1$H-NMR (CDCl$_3$) δ: 1.01 (1H, m), 1.21 (3H, s), 1.65 (3H, s), 1.66 (1H, s), 1.74 (3H, s), 2.0–2.4 (5H, m), 2.52 (1H, d, J=4.2 Hz), 2.55 (1H, t, J=6.4 Hz), 2.95 (1H, d, J=4.2 Hz), 3.41 (3H, s), 3.59 (1H, dd, J=11.2 Hz, J=2.6 Hz), 4.17 (1H, m), 4.68 (1H, d, J=10.2 Hz), 4.74 (1H, d, J=8.8 Hz), 4.80 (1H, d, J=8.8 Hz), 4.85 (1H, d, J=10.2 Hz), 7.2–7.45 (4H, m).

EXAMPLE 49

O-(4-Chlorobutyryl)fumagillol

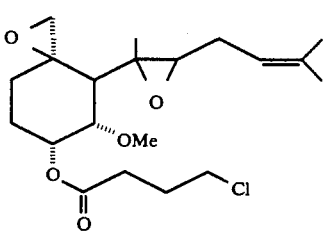

To a solution of fumagillol (300 mg) and dimethylaminopyridine (260 mg) in anhydrous dichloromethane (5 ml) was added dropwise 4-chlorobutyryl chloride (0.14 ml) under ice cooling and the mixture was stirred at room temperature for 1 hour. The reaction mixture was diluted with ethyl acetate, washed with saturated aqueous sodium hydrogen carbonate solution and saturated aqueous sodium chloride solution and drived over anhydrous magnesium sulfate. The solvent was distilled off under reduced pressure and the residue was subjected to silica gel column chromatography, elution being carried out with a mixture of n-hexane and ethyl acetate (1:4). The eluate was concentrated under reduced pressure to give O-(4-chlorobutyryl)-fumagillol (311 mg) as a colorless oil.

$^1$H-NMR (CDCl$_3$) δ: 1.10 (1H, s), 1.21 (3H, s), 1.66 (3H, s), 1.75 (3H, s), 1.80–2.45 (7H, m), 2.58 (4H, m), 2.99 (1H, d, J=4.2 Hz), 3.43 (3H, s), 3.61 (2H, t, J=6.4 Hz), 3.64 (1H, dd, J=2.8 Hz, J=11.4 Hz), 5.21 (1H, m), 5.68 (1H, m).

EXAMPLE 50

O-(N-Methylsulfamoyl)fumagillol

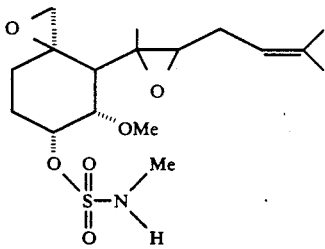

To a solution of fumagillol (300 mg) and dimethylaminopyridine (400 mg) in anhydrous dichloromethane (2 ml) was added dropwise N-methylsulfamoyl chloride (0.30 ml) and the mixture was stirred at room temperature for 20 minutes. The reaction mixture was diluted with ethyl acetate, washed with saturated aqueous sodium hydrogen carbonate solution and saturated aqueous sodium chloride solution and dried over anhydrous magnesium sulfate. The solvent was distilled off under reduced pressure and the residue was subjected to silica gel column chromatography, elution being carried out with a mixture of n-hexane and ethyl acetate (1:2). The eluate was concentrated under reduced pressure to give O-(N-methylsulfamoyl)fumagillol (367 mg) as colorless crystals. A portion of the above crop of crystals was recrystallized from isopropyl ether for melting point determination.

m.p.: 108°–109° C.

$^1$H-NMR (CDCl$_3$) δ: 1.12 (1H, s), 1.20 (3H, s), 1.66 (3H, s), 1.75 (3H, s), 1.95(1H, d, J=11.4 Hz), 1.85–2.45 (4H, m), 2.58 (1H, t, J=6.6 Hz), 2.60 (1H, d, J=4.0 Hz), 2.80 (3H, d, J=5.2 Hz), 2.99 (1H, d, J=4.0 Hz), 3.56 (3H, s), 3.68 (1H, dd, J=2.0 Hz, J=11.4 Hz), 5.15–5.30 (3H, m).

EXAMPLE 51

O-Chloroacetylcarbamoyldihydrofumagillol

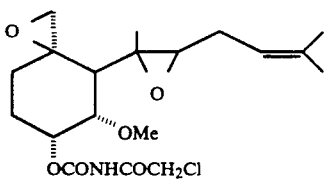

O-Chloroacetylcarbamoyldihydrofumagillol (173 mg) (81% yield) was derived from dihydrofumagillol (150 mg) in the same manner as in Example 8.

$^1$H-NMR (CDCl$_3$) δ: 0.91 (6H, d, J=6.6 Hz), 1.13 (1H, m), 1.18 (3H, s), 1.2–2.2 (9H, m), 2.57 (1H, dd, J=7.2 Hz, J=4.6 Hz), 2.63 (1H, d, J=4.2 Hz), 2.91 (1H, d, J=4.2 Hz), 3.47 (3H, s) 3.69 (1H, dd, J=11.4 Hz, J=2.6 Hz), 4.44 (2H, s), 5.62 (1H, br s), 8.36 (1H, br s).

EXAMPLE 52

O-[[1-(2-Dimethylaminoethyl)tetrazol]-5-yl-thioacetylcarbamoyl]fumagillol

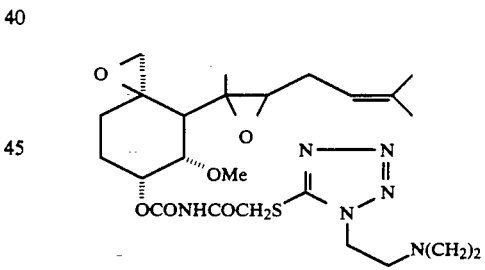

In the same manner as in Example 42, O-chloroacetylcarbamoylfumagillol (195 mg) was reacted with 1-(2-dimethylaminoethyl)-5-mercaptotetrazole sodium (113 mg) with stirring at room temperature for 1 hour. Purification by silica gel column chromatography (eluent: ethyl acetate) gave colorless, powdery O-[[1-(2-dimethylaminoethyl)tetrazol]-5-yl-thioacetylcarbamoyl]fumagillol (217 mg) (83% yield).

$^1$H-NMR (CDCl$_3$) δ: 1.10 (1H, m), 1.20 (3H, s), 1.66 (3H, s), 1.75 (3H, s), 1.8–2.45 (6H, m), 2.59 (2H, m), 2.77 (2H, t, J=6.2 Hz), 2.99 (1H, d, J=4.2 Hz, 3.47 (3H, s), 3.67 (1H, dd, J=11.4 Hz, J=2.6 Hz), 4.37 (4H, m), 5.20 (1H, m), 5.62 (1H, m), 8.99 (1H, br s).

EXAMPLE 53

O-[(2-methyl-1,3,4-thiadiazol-5-yl)thioacetylcarbamoyl]fumagillol

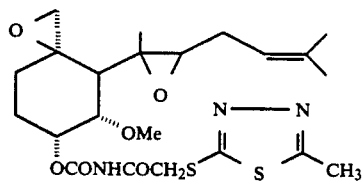

In the same manner as in Example 42, O-chloroacetylcarbamoylfumagillol (283 mg) was reacted with sodium 2-methyl-1,3,4-thiadiazole-5-thiolate (130 mg) with stirring at room temperature for 30 minutes. Purification by silica gel column chromatography (eluent: n-hexane-ethyl acetate=1:1) gave colorless, powdery O-[(2-methyl-1,3,4 -thiadiazol-5-yl)thioacetylcarbamoyl]fumagillol (293 mg) (84% yield).

$^1$H-NMR (CDCl$_3$) δ: 1.09 (1H, m), 1.20 (3H, s), 1.66 (3H, s), 1.75 (3H, s), 1.6–2.4 (6H, m), 2.57 (2H, m), 2.73 (3H, s), 2.98 (1H, d, J=4.2 Hz), 3.45 (3H, s), 3.67 (1H, dd, J=11.2 Hz, J=2.6 Hz), 4.32 (1H, d, J=16.2 Hz), 4.44 (1H, d, J=16.2 Hz), 5.21 (1H, m), 5.61 (1H, br s), 9.43 (1H, br s).

EXAMPLE 54

O-(1-Naphthalenethioacetylcarbamoyl)fumagillol

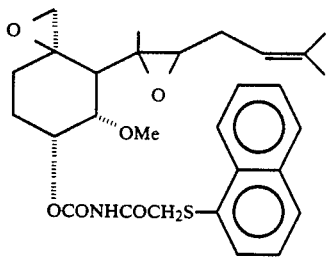

In the same manner as in Example 42, O-chloroacetylcarbamoylfumagillol (159 mg) was reacted with sodium naphthalenethiolate (188 mg) with stirring at room temperature for 5 minutes. Purification by silica gel column chromatography (eluent: n-hexane-ethyl acetate=3:1) gave colorless, powdery O-(1-naphthalenethioacetylcarbamoyl)fumagillol (160 mg) (81% yield).

$^1$H-NMR (CDCl$_3$) δ: 1.08 (1H, m), 1.20 (3H, s), 1.66 (3H, s), 1.75 (3H, s), 1.89 (1H, d, J=11.2 Hz), 1.6–2.45 (5H, m), 2.54 (2H, m), 2.73 (3H, s), 2.98 (1H, d, J=4.2 Hz), 3.45 (3H, s), 3.66 (1H, dd, J=11.2 Hz, J=2.6 Hz), 3.96 (1H, d, J=15.4 Hz), 4.07 (1H, d, J=15.4 Hz), 5.20 (1H, M), 5.57 (1H, m), 7.35–7.9 (6H, m), 8.11 (1H, br s), 8.40 (1H, d, J=7.8 Hz).

EXAMPLE 55

O-[(N-Methylpyrrolidin-1-ylium)acetylcarbamoyl]fumagillol chloride

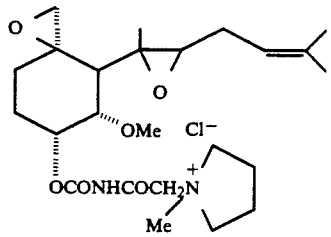

O-Chloroacetylcarbamoylfumagillol (170 mg) and N-methylpyrzolidine (1 ml) were stirred in ether (3 ml) at room temperature for 1 week. The resultant precipitate was recovered by filtration, washed with ether and dried in vacuo. The procedure gave colorless, powdery O-[(N-methylpyrrolidin-1-ylium)acetylcarbamoyl]fumagillol chloride (170 mg) (82% yield).

$^1$H-NMR (CDCl$_3$) δ: 0.97 (1H, m), 1.16 (3H, s), 1.63 (3H, s), 1.73 (3H, s), 1.4–2.7 (1H, m), 2.53 (1H, d, J=4.2 Hz), 2.66 (1H, t, J=6.2 Hz), 2.94 (1H, d, J=4.2 Hz), 3.41 (3H, s), 3.42 (2H, s), 3.64 (1H, dd, J=11.4 Hz, J=2.6 Hz), 3.8–4.1 (4H, m), 4.70 (1H, d, J=16.8 Hz), 5.14 (1H, m), 5.40 (1H, d, J=16.8 Hz), 5.60.

EXAMPLE 56

O-[2-(N,N,N-Trimethylammonio)ethylcarbamayl]fumagillol iodide

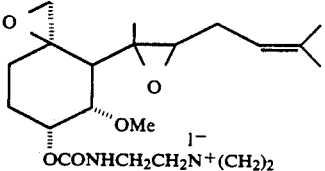

O-(2-Dimethylaminoethylcarbamoyl)fumagillol (81 mg) and methyl iodide (0.5 ml) were stirred in dichloromethane (1 ml) at room temperature for 15 hours. The solvent was distilled off under reduced pressure and the residue was washed with ether to give colorless, powdery O-[2-(N,N,N-trimethylammonio)ethylcarbamoyl]fumagillol iodide (105 mg) (95% yield).

m.p.: 94°–95° C.

$^1$H-NMR (CDCl$_3$) δ: 1.03 (1H, m), 1.17 (3H, s), 1.66 (3H, s), 1.75 (3H, s), 1.5–2.4 (6H, m), 2.57 (1H, d, J=4.2 Hz), 2.68 (1H, t, J=6.6 Hz), 2.97 (1H, d, J=4.2 Hz), 3.44 (12H, s), 3.3–3.9 (5H, m), 5.18(1H, m), 5.50 (1H, m) 6.80 (1H, m).

EXAMPLE 57

O-[N-Acetyl-(2-dimethylaminoethylcarbamoyl)-]fumagillol

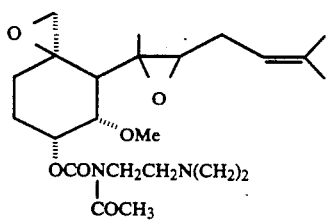

To a solution of O-(2-dimethylaminoethylcarbamoyl)fumagillol (145 mg) and triethylamine (0.5 ml) in dichloromethane (2 ml) was added acetic anhydride (0.3 ml) and the mixture was stirred at room temperature for 1 day. The reaction mixture was diluted with ethyl acetate, washed with water and saturated aqueous sodium chloride solution and dried over anhydrous magnesium sulfate. The solvent was distilled off under reduced pressure and the residue was purified by silica gel column chromatography (eluent: dichloromethane-methanol=20:1) to give colorless, oily O-[N-acetyl-(2-dimethylaminoethylcarbamoyl]fumagillol (113 mg) (73% yield).

$^1$H-NMR (CDCl$_3$) δ: 1.15 (1H, m), 1.20 (3H, s), 1.65 (3H, s), 1.74 (3H, s), 1.95 (3H, s), 1.9–2.6 (7H, m), 2.50 (3H, s), 2.53 (3H, s), 2.60 (1H, d, J=4.4 Hz), 2.78 (1H, t, J=6.4 Hz), 2.86 (1H, m), 3.02 (1H, t, J=6.4 Hz), 3.45 (3H, s), 3.69 (1H, dd, J=11.4 Hz, J=2.8 Hz), 4.03 (2H, m), 5.20 (1H, m), 5.71 (1H, m).

EXAMPLE 58

O-Acryloylcarbamoylfumagillol

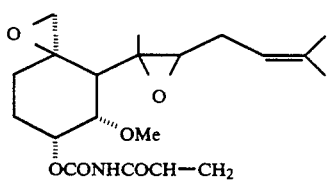

In the same manner as in Example 8, fumagillol (220 mg) was reacted with acryloyl isocyanate (200 mg) with stirring at room temperature for 30 minutes. Purification by silica gel column chromatography (eluent: n-hexane-ethyl acetate=3:1) gave colorless, powdery O-acryloylcarbamoylfumagillol (60 mg) (21% yield).

$^1$H-NMR (CDCl$_3$) δ: 1.10 (1H, m), 1.21 (3H, s), 1.66 (3H, s), 1.75 (3H, s), 1.6–2.5 (6H, m), 2.58 (1H, d, J=4.2 Hz), 2.59 (1H, m), 2.99 (1H, d, J=4.2 Hz), 3.47 (3H, s), 3.69 (1H, dd, J=11.2 Hz, J=2.6 Hz), 5.21 (1H, m), 5.60 (1H, m), 5.88 (1H, dd, J=10.4 Hz, J=1.6 Hz), 6.51 (1H, dd, J=17.0 Hz, J=1.6 Hz), 6.92 (1H, dd, J=17.0 Hz, J=1.6 Hz), 6.92 (1H, dd, J=17.0 Hz, J=10.4 Hz), 7.78 (1H, br s).

EXAMPLE 59

O-[(1-Methyl-2-methoxycarbonyl-1, 3, 4-triazol-5-yl)thioacetylcarbamoyl]fumagillol

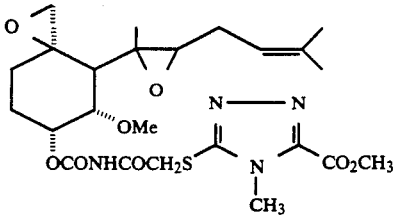

In the same manner as in Example 42, O-chloroacetylcarbamoylfumagillol (270 mg) was reacted with sodium 1-methyl-2-methoxycarbonyl-1,3,4-triazole-5-thiolate (164 mg) with stirring at room temperature for 30 minutes. Purification by silica gel column chromatography (eluent: n-hexane-ethyl acetate=1:4) gave colorless, powdery O-[(1-methyl-2-methoxycarbonyl-1,3,4-triazol-5-yl)thioacetylcarbamoyl)fumagillol (288 mg) (80% yield).

$^1$H-NMR (CDCl$_3$) δ: 1.07 (1H, m), 1.18 (3H, s), 1.65 (3H, s), 1.75 (3H, s), 1.6–2.4 (6H, m), 2.54 (2H, 2.96 (1H, d, J=4.2 Hz), 3.44 (3H, s), 3.64 (1H, dd, J=11.4 Hz, J=2.4 Hz), 3.91 (3H, s), 3.99 (3H, s) 4.30 (1H, d, J=15.8 Hz), 4.41 (1H, d, J=15.8 Hz), 5.19 (1H, m), 5.59 (1H, m), 9.96 (1H, br s).

EXAMPLE 60

O-[(2-Benzoxazolyl)thioacetylcarbamoyl]fumagillol

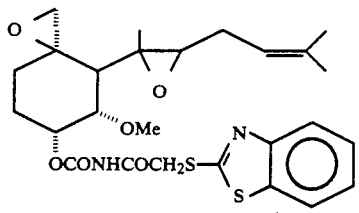

In the same manner as in Example 42, O-chloroacetylcarbamoylfumagillol (230 mg) was reacted with 2-mercaptobenzoxazole sodium salt (119 mg) with stirring at room temperature for 30 minutes. Purification by silica gel column chromatography (eluent: n-hexane-ethyl acetate=3:1) gave colorless, powdery O-[(2-benzoxazolyl)thioacetylcarbamoyl]fumagillol (269 mg) (91% yield)

$^1$H-NMR (CDCl$_3$) δ: 1.04 (1H, m), 1.20 (3H, s), 1.66 (3H, s), 1.75 (3H, s), 1.8–2.6 (8H, m), 2.97 (1H, d, J=4.4 Hz), 3.47 (3H, s), 3.67 (1H, dd, J=11.2 Hz, J=2.6 Hz), 4.31 (2H, s), 5.20 (1H, m), 5.63 (1H, m), 7.2–7.3 (2H, m), 7.47 (1H, m), 7.58 (1H, m), 9.49 (1H, br s).

EXAMPLE 61

O-[(2-Benzoimidazolyl)thioacetylcarbamoyl]fumagillol

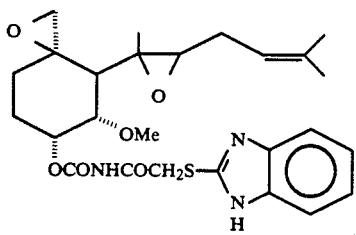

In the same manner as in Example 42, O-chloroacetylcarbamoylfumagillol (257 mg) was reacted with 2-mercaptobenzoimidazole sodium salt (132 mg) with stirring at room temperature for 30 minutes. Purification by silica gel column chromatography (eluent: n-hexane-ethyl acetate=1:1) gave colorless, powdery O-[(2-benzoimidazolyl)thioacetylcarbamoyl]fumagillol (297 mg) (90% yield).

$^1$H-NMR (CDCl$_3$) δ: 1.03 (1H, m), 1.19 (3H, s), 1.71 (3H, s), 1.83 (3H, s), 1.6–2.4 (7H, m), 2.57 (1H, d, J=4.4 Hz), 2.96 (1H, d, J=4.4 Hz), 3.46 (3H, s), 3.68 (1H, dd, J=11.6 Hz, J=2.2 Hz), 3.74 (1H, d, J=14.2 Hz), 3.87 (1H, d, J=14.2 Hz), 5.25 (1H, m), 5.69 (1H, m), 7.10 (2H, m), 7.3–7.5 (2H, m), 11.01 (1H, br s), 12.60 (1H, br s).

EXAMPLE 62

O-[(8-Quinolyl)thioacetylcarbamoyl]fumagillol

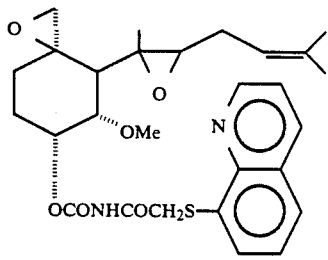

In the same manner as in Example 42, O-chloroacetylcarbamoylfumagillol (289 mg) was reacted with 8-mercaptoquinoline sodium salt (208 mg) with stirring at room temperature for 30 minutes. Purification by silica gel column chromatography (eluent: n-hexane-ethyl acetate=7:3) gave colorless, powdery O-[(8-quinolyl)thioacetylcarbamoyl]fumagillol (382 mg) (99% yield).

$^1$H-NMR (CDCl$_3$) δ: 1.07 (1H, m), 1.25 (3H, s), 1.65 (3H, s), 1.75 (3H, s), 1.6–2.55 (8H, m), 2.95 (1H, d, J=4.2 Hz), 3.51 (3H, s), 3.74 (1H, dd, J=11.4 Hz, J=2.8 Hz), 3.77 (1H, d, J=15.4 Hz), 3.92 (1H, d, J=15.4 Hz), 5.19 (1H, m), 5.67 (1H, m), 7.50 (1H, t, J=7.8 Hz), 7.60 (1H, dd, J=8.4 Hz, J=4.4 Hz), 7.82 (1H, d, J=7.8 Hz), 7.91 (1H, d, J=7.2 Hz), 8.26 (1H, dd, J=8.4 Hz, j=1.6 Hz), 9.20 (1H, dd, J=4.4 Hz, J=1.6 Hz), 11.84 (1H, br s).

EXAMPLE 63

O-[(2-Pyridyl)thioacetylcarbamoyl]fumagillol

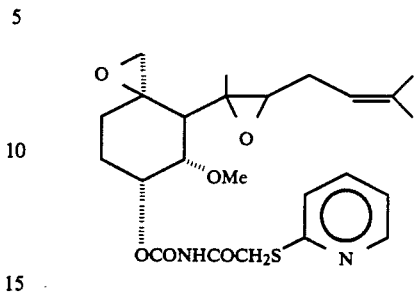

In the same manner as in Example 42, O-chloroacetylcarbamoylfumagillol (292 mg) was reacted with 2-pyridinethiol sodium salt (116 mg) with stirring at room temperature for 30 minutes. Purification by silica gel column chromatography (eluent: n-hexane-ethyl acetate=2:1) gave colorless, powdery O-[(2-pyridyl)thioacetylcarbamoyl]fumagillol (325 mg) (94% yield).

$^1$H-NMR (CDCl$_3$) δ: 1.08 (1H, m), 1.21 (3H, s), 1.67 (3H, s), 1.76 (3H, s), 1.6–2.6 (8H, m), 2.98 (1H, d, J=4.2 Hz), 3.47 (3H, s), 3.66 (1H, dd, J=11.2 Hz, J=2.6 Hz), 3.77 (1H, d, J=14.8 Hz), 3.93 (1H, d, J=14.8 Hz), 5.23 (1H, m), 5.60 (1H, m), 7.11 (1H, m), 7.31 (1H, d, J=8.8 Hz), 7.59 (1H, m), 8.45 (1H, d, J=5.0 Hz) 10.67 (1H, br s).

EXAMPLE 64

O-[(4-Pyridyl)thioacetylcarbamoyl]fumagillol

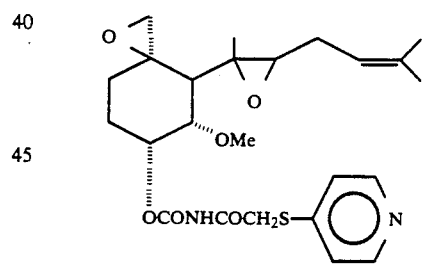

In the same manner as in Example 42, O-chloroacetylcarbamoylfumagillol (290 mg) was reacted with 4-pyridinethiol sodium salt (115 mg) with stirring at room temperature for 30 minutes. Purification by silica gel column chromatography (eluent: n-hexane-ethyl acetate=1:2) gave colorless, powdery O-[(4-pyridyl)thioacetylcarbamoyl]fumagillol (314 mg) (91% yield).

$^1$H-NMR (CDCl$_3$) δ: 1.10 (1H, m), 1.21 (3H, s), 1.66 (3H, s), 1.75 (3H, s)., 1.6–2.6 (6H, m), 2.54 (1H, t, J=6.2 Hz), 2.57 (1H, d, J=4.4 Hz), 2.98 (1H, d, J=4.4 Hz), 3.48 (3H, s), 3.69 (1H, dd, J=11.2 Hz, J=2.4 Hz), 4.13 (1H, d, J=15.8 Hz), 4.22 (1H, d, J=15.8 Hz), 5.20 (1H, m), 5.61 (1H, m), 7.22 (2H, dd, J=5.0 Hz, J=1.4 Hz), 8.43 (2H, d, J=6.0 Hz), 8.82 (1H, br s).

EXAMPLE 65

O-(Methylthioacetylcarbamoyl)fumagillol

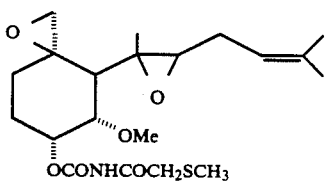

In the same manner as in Example 42, O-chloroacetylcarbamoylfumagillol (107 mg) was reacted with methanethiol sodium salt (225 mg) with stirring at 10° C. for 1 hour. Purification by silica gel column chromatography (eluent: n-hexane-ethyl acetate=3:1) gave colorless, powdery O-(methylthioacetylcarbamoyl)fumagillol (500 mg) (4516 yield).

$^1$H-NMR (CDCl$_3$) δ: 1.10 (1H, m), 1.21 (3H, s), 1.66 (3H, s), 1.75 (3H, s), 1.75 (3H, s), 1.93 (1H, d, J=11.2 Hz), 2.18 (3H, s), 1.7–2.45 (5H, m), 2.58 (2H, m), 2.99 (1H, d, J=4.2 Hz), 3.47 (3H, s), 3.48 (1H, d, J=16.8 Hz), 3.55 (1H, d, J=16.8 Hz), 3.68 (1H, dd, J=11.2 Hz, J=2.8 Hz), 5.20 (1H, m), 5.61 (1H, m), 8.12 (1H, br s).

EXAMPLE 66

O-[(4-Hydroxypyrimidin-2-yl)thioacetylcarbamoyl]-fumagillol

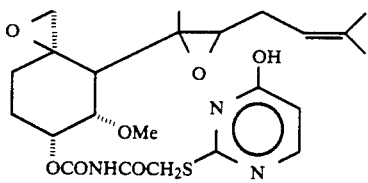

In the same manner as in Example 42, O-chloroacetylcarbamoylfumagillol (239 mg) was reacted with thiouracil sodium salt (123 mg) with stirring at room temperature for 30 minutes. Purification by silica gel column chromatography (eluent: n-hexane-ethyl acetate=1:5) gave colorless, powdery O-[(4-hydroxypyrimidin-2-yl)thioacetylcarbamoyl]fumagillol (208 mg) (71% yield).

$^1$H-NMR (CDCl$_3$) δ: 1.09 (1H, m), 1.22 (3H, s), 1.66 (3H, s), 1.75 (3H, s), 1.5–2.6 (7H. m), 2.58 (1H, d, is J=4.2 Hz), 2.99 (1H, d, J=4.2 Hz), 3.47 (3H, s), 3.68 (1H, dd, J=11.2 Hz, J=2.4 Hz), 4.08 (1H, d, J=15.8 Hz), 4.20 (1H, d, J=15.8 Hz), 5.21 (1H, m), 5.61 (1H, M), 6.27 (1H, d, J=6.6 Hz), 7.88 (1H, d, J=6.6 Hz), 9.07 (1H, br s).

EXAMPLE 67

O-[(1,2,3-Triazol-5-yl)thioacetylcarbamoyl]fumagillol

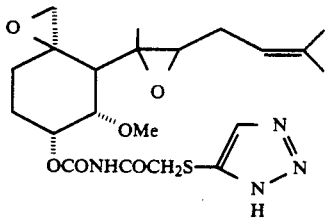

In the same manner as in Example 42, O-chloroacetylcarbamoylfumagillol (249 mg) was reacted with 5-mercapto-1,2,3-triazole sodium salt (118 mg) with stirring at room temperature for 1 hour. Purification by silica gel column chromatography (eluent: n-hexane-ethyl acetate=3:2) gave colorless, powdery O-[(1,2,3-triazol-5-yl)thioacetylcarbamoyl]fumagillol (206 mg) (71% yield).

$^1$H-NMR (CDCl$_3$) δ: 1.07 (1H, m), 1.27 (3H, s), 1.67 (3H, s), 1.76 (3H, s), 1.7–2.6 (6H, m), 2.59 (1H, d, J=4.2 Hz), 2.79 (1H, t, J=6.2 Hz), 2.99 (1H, d, J=4.2 Hz), 3.41 (3H, s), 3.69 (1H, dd, J=11.2 Hz, J=2.6 Hz), 3.3–3.9 (2H, m), 5.20 (1H, m), 5.59 (1H, m), 7.71 (1H, s), 8.90 (1H, br s).

EXAMPLE 68

O-[(Dimethylsulfonio)acetylcarbamoyl]fumagillol iodide

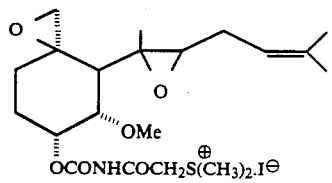

O-(Methylthioacetylcarbamoyl)fumagillol (167 mg) and methyl iodide (1 ml) were stirred in acetonitrile (1 ml) at room temperature overnight. The solvent was distilled off under reduced pressure and ether was added to the residue. The resulting precipitate was collected by filtration, washed with ether and dried under reduced pressure to give colorless, powdery O-[(dimethylsulfonio)acetylcarbamoyl]fumagillol iodide (79 mg) (35% yield).

$^1$H-NMR (d$_6$-DMSO) δ: 1.09 (3H, s), 1.32 (1H, m), 1.62 (3H, s), 1.72 (3H, s), 1.6–2.95 (10H, m), 2.92 (6H, s), 3.34 (3H, s), 3.66 (1H, m), 4.90 (2H, s), 5.21 (1H, m), 5.49 (1H, m).

EXAMPLE 69

O-[(N-Methylpyridin-4-ylium)thioacetylcarbamoyl]-fumagillol iodide

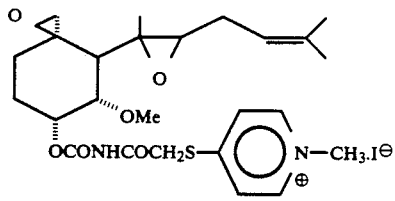

O-[(4-Pyridyl)thioacetylcarbamoyl]fumagillol (113 mg) and methyl iodide (1 ml) were dissolved in dichloromethane (2 ml) and the solution was stirred at room temperature overnight. The solvent was distilled off under reduced pressure and ether was added to the residue. The resulting precipitate was collected by filtration and washed with ether to give colorless, powdery O-( (N-methylpyridin-4-ylium)thioacetylcarbamoyl]fumagillol iodide (127 mg) (87% yield).

$^1$H-NMR (CDCl$_3$) δ: 1.05 (1H, m), 1.21 (3H, s), 1.65 (3H, s), 1.74 (3H, s), 1.5–2.65 (7H, m), 2.92 (1H, t, J=6.2 Hz), 2.98 (1H, d, J=4.0 Hz), 3.49 (3H, s), 3.71 (1H, dd, J=11.2 Hz, J=2.4 Hz), 4.32 (2H, m), 4.37 (3H, s), 5.19

(1H, m), 5.64 (1H, m), 7.90 (2H, d, J=6.8 Hz), 3.76 (2H, d, J=6.8 Hz), 10 12 (1H, br s).

EXAMPLE 70

O-[N-(Ethoxycarbonyl)carbamoyl]fumagillol

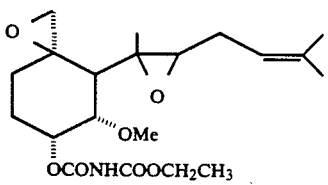

In the same manner as in Example 8, fumagillol (350 mg) was reacted with ethoxycarbonyl isocyanate (200 mg) with stirring at room temperature for 30 minutes. Purification by silica gel column chromatography (eluent: n-hexane-ethyl acetate=3:1) gave colorless, powdery O-[N-(ethoxycarbonyl)carbamoyl]fumagillol (370 mg) (75% yield).

$^1$H-NMR (CDCl$_3$) δ: 1.08 (1H, m), 1.21 (3H, s), 1.30 (3H, t, J=7.0 Hz), 1.66 (3H, s), 1.75 (3H, s), 1.8–2.45 (EH, m), 2.56 (1H, d, J=4.2 Hz), 2.57 (1H, m), 2.98 (1H, d, J=4.2 Hz), 3.46 (3H, s), 3.67 (1H, dd, J=11.4 Hz, J=2.8 Hz), 4.23 (2H, q, J=7.0 Hz), 5.21 (1H, m), 5.62 (1H, m), 7.21 (1H, br s).

EXAMPLE 71

O-(3-Furoyl)fumagillol

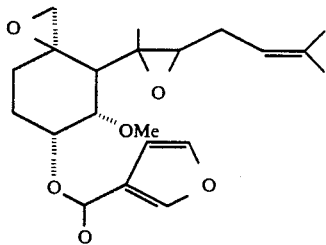

In dichloromethane (15 ml) was dissolved 3-furancarboxylic acid (397 mg) followed by addition of oxalyl chloride (0.62 ml) and the mixture was refluxed for 1 hour. After cooling, the solvent was distilled off under reduced pressure to give crude 3-furancarbonyl chloride. In dichloromethane (2 ml) were dissolved fumagillol (500 mg) and dimethylaminopyridine (433 mg), and under ice-cooling, a solution of the above 3-furanecarbonyl chloride in dichloromethane (5 ml) was added dropwise. Then, at room temperature, the mixture was stirred for 30 minutes. Thereafter, the reaction mixture was diluted with ethyl acetate (50 ml), then washed successively with 10% aqueous citric acid solution, saturated aqueous sodium chloride solution, saturated aqueous sodium hydrogen carbonate solution and saturated aqueous sodium chloride solution, and dried over anhydrous magnesium sulfate. Finally, the solvent was distilled off under reduced pressure and the residue was purified by silica gel column chromatography (eluent: n-hexane-ethyl acetate=1:1) to give 187 mg of O-(3-furoyl)fumagillol as colorless oil (28% yield).

$^1$H-NMR (CDCl$_3$) δ: 1.25 (1H, m), 1.23 (3H, s), 1.66 (3H, s), 1.75 (3H, s), 1.8–2.5 (5H, m), 1.98 (1H, d, J=11 Hz), 2.58 (1H, d, J=4 Hz), 2.61 (1H, t, J=7 Hz), 3.02 (1H, d, J=4 Hz), 3.47 (3H, s), 3.72 (1H, dd, J=3 Hz, J=11 Hz), 5.21 (1H, m), 5.81 (1H, m), 6.72 (1H m), 7.41 (1H, m), 8.00 (1H, m).

EXAMPLE 72

O-[N-(3-Furoyl)carbamoyl]fumagillol

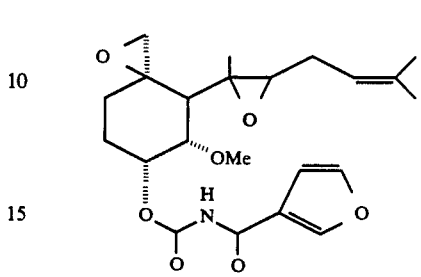

3-Furancarboxamide (167 mg) was suspended in dichloromethane (10 ml), followed by addition of oxalyl chloride (0.20 ml) under ice-cooling, and the temperature of the reaction mixture was raised to room temperature. The reaction mixture was refluxed for 10 hours and the solvent was distilled off to give crude 3-furoyl isocyanate. In the same manner as in Example 8, the above product was reacted with fumagillol (213 mg) with stirring at room temperature for 30 minutes. Purification by silica gel column chromatography (eluent: n-hexane-ethyl acetate=2:1) gave colorless, powdery O-[N-(3-furoyl)carbamoyl]fumagillol (120 mg) (38% yield).

$^1$H-NMR (CDCl$_3$) δ: 1.11 (1H, m), 1.22 (3H, s), 1.66 (3H, s), 1.75 (3H, s), 1.8–2.5 (5H, m), 2.00 (1H, d, J=11.2 Hz), 2.57 (1H, d, J=4.0 Hz), 2.61 (1H, t, J=6.6 Hz), 2.99 (1H, d, J=4.0 Hz), 3.44 (4H, m), 3.70 (1H, dd, J=11.2 Hz, J==2.8 Hz), 5.20 (1H, m), 5.63 (1H, m), 6.80 (1H, m), 7.47 (1H, m), 8.16 (1H, m), 8.26 (1h br s).

EXAMPLE 73

O-[N-(Phenoxycarbonyl)carbamoyl]fumagillol

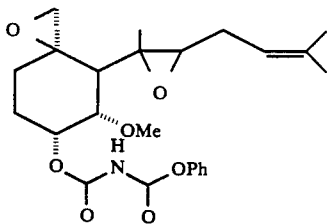

In the same manner as in Example 8, fumagillol (200 mg) was reacted with phenoxycarbonyl isocyanate (231 mg) with stirring at room temperature for 4 hours. Purification by silica gel column chromatography (eluent: n-hexane-ethyl acetate=2:1) gave colorless, powdery O-[N-(phenoxycarbonyl)carbamoyl]fumagillol (125 mg) (39% yield).

$^1$H-NMR (CDCl$_3$) δ: 1.09 (1H, m), 1.21 (3H, s), 1.65 (3H, s), 1.74 (3H, s), 1.5–2.5 (6H, m), 2.55 (1H, d, J=4.1 Hz), (2.57 (1H, t, J=6.5 Hz), 2.98 (1H, d, J=4.1 Hz), 3.50 (3H, s), 3.69 (1H, dd, J=1.4 Hz, J=11.2 Hz), 5.20 (1H, m), 5.70 (1H, m), 7.1–7.4 (5H, m), 7.66 (1H, br s).

EXAMPLE 74

O-(N'-Chloroacetylallophanoyl)fumagillol

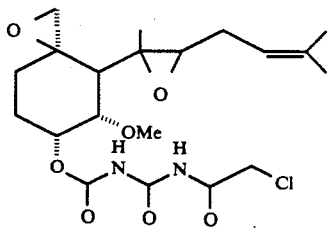

O-Carbamoylfumagillol (200 mg) was dissolved in dichloromethane (4 ml) followed by addition of chloroacetyl isocyanate (0.10 ml) and the mixture was stirred for 4 hours. The reaction mixture was diluted with ethyl acetate (50 ml), washed with saturated aqueous sodium hydrogen carbonate solution and saturated aqueous sodium chloride solution and dried over anhydrous magnesium sulfate. The solvent was distilled off under reduced pressure and the residue was purified by silica gel column chromatography (eluent: n-hexane-ethyl acetate=1) to give colorless, powdery O-(N'-chloroacetylallophanoyl)fumagillol (230 mg) (84% yield).

$^1$H-NMR (CDCl$_3$) δ: 1.12 (1H, m), 1.21 (3H, s), 1.66 (3H, s), 1.75 (3H, s), 1.8-2.5 (6H, m), 1.92 (1H, d, J=11.2 Hz), 2.57 (1H, d, J=4.2 Hz), 2.59 (1H, t, J=6.8 Hz), 2.99 (1H, d, J=4.2 Hz), 3.48 (3H, s), 3.68 (1H, dd, J=11.4 Hz, J=2.8 Hz), 4.39 (2H, s), 5.20 (1H, m), 5.65 (1H, m).

EXAMPLE 75

O-(N'-Benzoylallophanoyl)fumagillol

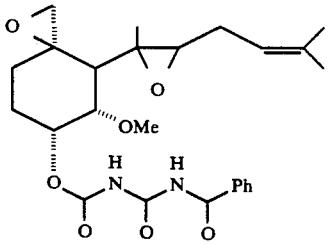

In the same manner as in Example 74, O-carbamoylfumagillol (200 mg) was reacted with benzoyl isocyanate (0.51 ml) with stirring at room temperature for 2 days. Purification by silica gel column chromatography (eluent: n-hexane-ethyl acetate=3:2) gave colorless, powdery O-(N'-benzoylallophanoyl)fumagillol (100 mg) (34% yield).

$^1$H-NMR (CDCl$_3$) δ: 1.12 (1H, m), 1.22 (1H, m), 1.23 (3H, s), 1.66 (3H, s), 1.75 (3H, s), 1.97 (1H, d, J=11.0 Hz), 1.8-2.5 (5H, m), 2.58 (1H, d, J=4.2 Hz), 2.62 (1H, t, J=6.8 Hz), 3.00 (1H, d, J=4.2 Hz), 3.50 (3H, s), 3.69 (1H, dd, J=11.0 Hz, J=2.6 Hz), 5.20 (1H, m), 5.72 (1H, br s), 7.5-7.7 (3H, m), 7.91 (2H, m)

EXAMPLE 76

O-Chloroacetylcarbamoyl-6'b-hydroxyfumagillol

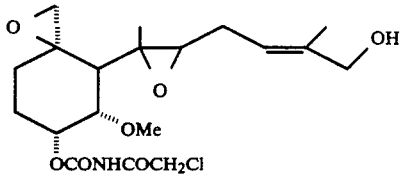

Selenium dioxide (295 mg) was added to a 954 solution of O-chloroacetylcarbamoylfumagillol (711 mg) in ethanol (30 ml) and the mixture was refluxed for 5 hours. The solvent was distilled off under reduced pressure. The residue was dissolved in ethyl acetate, washed with saturated aqueous sodium hydrogen carbonate solution and saturated aqueous sodium chloride solution and dried over anhydrous magnesium sulfate. The solvent was distilled off under reduced pressure and the residue was purified by silica gel column chromatography to give colorless, powdery O-chloroacetylcarbamoyl-6'b-hydroxyfumagillol (190 mg) (26% yield).

$^1$H-NMR (CDCl$_3$) δ: 1.13 (1H, m), 1.22 (3H, s), 1.70 (3H, s), 1.6-2.5 (5H, m), 1.93 (1H, d, J=11.2 Hz), 2.60 (2H, d, J=4.2 Hz), 2.63 (1H, t, J=6.3 Hz), 2.94 (1H, d, J=4.2 Hz), 3.47 (3H, s), 3.69 (1H, dd, J=11.2 Hz, J=2.8 Hz), 4.05 (2H, d, J=5.8 Hz), 5.53 (1H, m), 5.61 (1H, m), 8.18 (1H, brs).

EXAMPLE 77

O-Chloroacetylcarbamoyl-6'b-dimethylaminofumagillol (a) O-Acetyl-6'b-hydroxyfumagillol

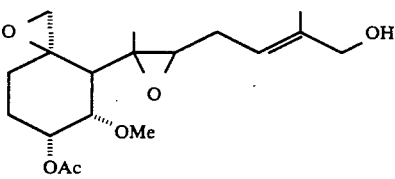

In the same manner as in Example 76, O-acetylfumagillol (1.00 g) was oxidized with selenium dioxide (0.68 g) and the oxidation product was purified by silica gel column chromatography (eluent: n-hexane-ethyl acetate=1:2) to give colorless, oily O-acetyl-6'b-hydroxyfumagillol (300 mg) (29% yield).

$^1$H-NMR (CDCl$_3$) δ: 1.12 (1H, m), 1.23 (3H, s), 1.71 (3H, s), 1.8-2.4 (5H, m), 1.95 (1H, d, J=11.2 Hz), 2.10 (3H, s), 2.57 (1H, d, J=4.2 Hz), 2.64 (1H, t, J=6.4 Hz), 2.93 (1H, d, J=4.2 Hz), 3.43 (3H, s), 3.64 (1H, dd, J=11.2 Hz, J=2.8 Hz), 4.05 (2H, brs), 5.54 (1H, m), 5.64 (1H, m).

(b) O-Acetyl-6'b-dimethylaminofumagillol

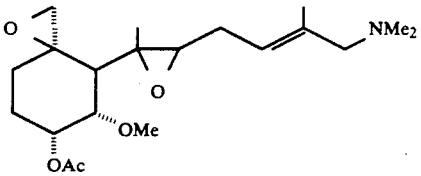

O-Acetyl-6'b-hydroxyfumagillol (469 mg) was dissolved in dichloromethane (5 ml) and, under ice-cooling, triethylamine (0.13 ml) and methanesulfonyl chloride (0.38 ml) were added to the solution. The mixture was stirred for 15 minutes. The reaction mixture was diluted with ethyl acetate (50 ml), washed with saturated aqueous sodium chloride solution and dried over anhydrous magnesium sulfate. The solvent was distilled off under reduced pressure and the residue was dissolved in dimethylformamide (5 ml). liner ice-cooling, anhydrous potassium carbonate (0.95 g) and dimethylamine hydrochloride (1.12 g) were added thereto. The temperature of the mixture was raised to room temperature and the mixture was stirred for 1 hour. The reaction mixture was diluted with ether (50 ml), washed with saturated aqueous sodium chloride solution and dried over anhydrous magnesium sulfate. The solvent was distilled off under reudced pressure and the residue was purified by silica gel column chromatography (eluent: chloroform-methanol-aqueous ammonia=20:1:0.1) to give colorless, oily O-acetyl-6'b-dimethylaminofumagillol (118 mg) (23% yield).

$^1$H-NMR (CDCl$_3$) δ: 1.08 (1H, m), 1.22 (3H, s), 1.71 (3H, s), 1.6–2.6 (5H, m), 1.96 (1H, d, J=11.2 Hz), 2.10 (3H, s), 2.18 (6H, s), 2.55 (1H, d, J=4.4 Hz)., 2.62 (1H, t, J=6.4 Hz), 2.81 (2H, br s), 2.95 (1H, d, J=4.4 Hz), 3.44 (3H, s), 3.65 (1H, dd, J=11.2 Hz, J=2.8 Hz), 5.41 (1H, m), 5.65 (1H, m).

(c) 6'b-Dimethylaminofumagillol

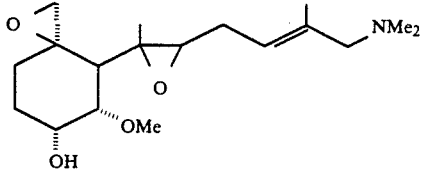

O-Acetyl-6'b-dimethylaminofumagillol (118 mg) was dissolved in methanol (2 ml), and 1N aqueous sodium hydroxide solution (1 ml) was added to the solution. The mixture was stirred for 15 minutes. The reaction mixture was diluted with ethyl acetate (50 ml), washed with saturated aqueous sodium chloride solution and dried over anhydrous magnesium sulfate. The solvent was distilled off under reduced pressure and the residue was purified by silica gel column chromatography (eluent: chloroform-methanol-aqueous ammonia=20:1:0.1) to give colorless, oily 6'b-dimethylaminofumagillol (102 mg) (97% yield).

$^1$H-NMR (CDCl$_3$) δ: 0.99 (1H, m), 1.23 (3H, s), 1.70 (3H. s), 1.6–2.5 (5H, m), 1.94 (1H, d, J=11.2 Hz), 2.17 (6H, s), 2.54 (1H, d, J=4.4 Hz), 2.62 (1H, t, J=6.4 Hz), 2.80 (2H, br s), 2.90 (1H, d, J=4.4 Hz), 3.50 (3H, s), 3.63 (1H, dd, J=11.2 Hz, J=2.8 Hz), 5.38 (1H, m), 5.40 (1H, m).

(d) O-Chloroacetylcarbamoyl-6'b-dimethylaminofumagillol

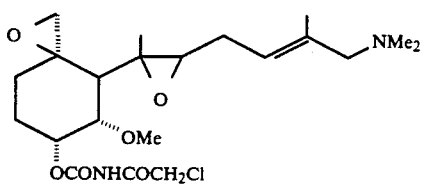

In the same manner as in Example 8, 6'b-dimethylaminofumagillol (152 mg) was reacted with chloroacetyl isocyanate (67 mg) with stirring at room temperature for 1 hour. Purification by silica gel column chromatography (eluent: chloroform-methanol-aqueous ammonia=20:1:0.1) gave colorless, powdery O-chloroacetylcarbamoyl-6'b-dimetylaminofumagillol (96 mg) (46% yield).

$^1$H-NMR (CDCl$_3$) δ: 1.12 (1H, m), 1.22 (3H, s), 1.70 (3H, s), 1.6–2.6 (6H, m), 2.58 (1H, d, J=4.2 Hz), 2.61 (1H, t, J=6.5 Hz), 2.18 (6H, s), 2.81 (2H, br s), 2.95 (1H, d, J=4.2 Hz), 3.47 (3H, s), 3.70 (1H, dd, J=11.2 Hz, J=2.8 Hz), 4.14 (2H, s), 5.40 (1H, m), 5.62 (1H, m).

EXPERIMENTAL EXAMPLE 2

Inhibition of Human Endothelial Cell Growth

Human umbilical vein endothelial cells (HUVE) were isolated by perfusion of an umbilical vein with a trypsin-containing medium. HUVE were cultured in GIT medium (Diago Eiyou Kagaku, Co., Japan) supplemented with 2.5% fetal bovine serum and 2.0 ng/ml of recombinant human basic fibroblast growth factor (rbFGF, Biotechnology Research Laboratories, Takeda, Osaka, Japan) at 370° C. under 5% CO$_2$ and 7% O$_2$. HUVE were plated on 96-well microtiter plates (Nunc, 1-67008) at the cell density of 2×10$^3$/100 μl of medium. The following day, 100 μl of medium containing rbFGF (2 ng/ml at the final concentration) and each compound (I) (shown by Example Numbers) at various concentrations were added to each well. The compounds (I) were dissolved in dimethylsulfoxide (DMSO) and then diluted with culture medium so that the final DMSO concentration does not exceed 0.25%. After 5-day culture, medium was removed, 100 μl of 1 mg/ml of MTT (3-(4,5-dimethyl-2-thiazolyl)- 2,5-diphenyl-2H-tetrazolium bromide) solution was added to wells, and microtiters were kept at 37° C. for 4 hours. Then, 100 μl of 10% sodium dodecyl sulfate (SDS) solution was added to wells, microtiters were kept at 37° for 5–6 hours. To determine the effects on cell number, the optical density (590 μm) of each well was measured using an optical densitometer. The concentration that exhibited 50% maximal inhibitory activity (IC$_{50}$) was calculated using the optical density of control wells as 100%.

TABLE 2

| Compounds (I) (Example No.) | (IC$_{50}$) (ng/ml) |
| --- | --- |
| 8 | 0.01 |
| 51 | 0.14 |
| 76 | 0.12 |

EXPERIMENTAL EXAMPLE 3

Suppression of Tumor-Formation In Vivo

The tumor used in this assay was mouse reticulum is cell sarcoma (M 5076), maintained by intraperitoneal transplantation into male C57BL/6N mice. The tumor cells in ascites were collected by centrifugation, and suspended in saline. The cell suspension (2×10$^6$ cells/100 μl/mouse) was inoculated into right flanks of mice. Tumor-bearing mice were subcutaneously treated with the compound (I) (shown by Example Numbers) suspended in 5% arabic gum solution containing 1% of ethanol, for 12 days beginning one day after tumor inoculation (10 injections). The tumor growth was determined by measuring tumor size in two directions with calipers at intervals of a few days. Results of tumor volumes one day after the final injection are shown in Table 3. The tumor volumes were calculated by the following formula. Tumor volume $(mm^3) = length \times (width)^2 \div 2$.

$$T/C\ (\%) = \frac{\text{tumor volumes of treated mice}}{\text{tumor volumes of control mice}} \times 100$$

TABLE 3

| Compound (I) 30 mg/day (Example No.) | T/C (%) |
|---|---|
| 8 | 14 |
| 51 | 22 |
| 76 | 29 |

In the following Experimental Examples 4–6, the fumagillol derivative compound (hereinafter "AGM-1470") described in Example 8 above was further evaluated for angiogenesis inhibitory activity.

EXPERIMENTAL EXAMPLE 4

Inhibition of Capillary Endothelial Cell Migration In Vitro:

The Boyden chamber assay was carried out using a modification of the method of Falk et al., J. Immunol. Meth., 33:239-247 (1980) as follows: Bovine capillary endothelial cells were plated at $1.5 \times 10^4$ cells per well in serum-free DMEM (Dulbecco's Modified Eagle's Medium) on one side of nucleopore filters precoated with fibronectin (7.3 μg fibronectin/ml PBS). AGM-1470 was dissolved in ethanol and diluted in DMEM so that the final concentration of ethanol did not exceed 0.01%. Cells were exposed to endothelial mitogen (Biomedical Technologies, Mass.) at 200 μg/ml and different concentrations of the AGM-1470 in serum-free DMEM for 4 hours at 37° C. At the end of this incubation, the number of cells that migrated through 8μ pores in the filters was determined by counting cells with an ocular grid at 100× in quadruplicate.

ACM-1470 completely inhibited cell migration in this assay when administered at a dose of 100 μg/ml. Significant inhibition of migration is observed at doses as low as 10 femptograms/ml. Half maximal inhibition of endothelial mitogen-induced migration approximately 100 pg/ml.

EXPERIMENTAL EXAMPLE 5

Inhibition of Angiogenesis in Chick Chorioallantoic Membranes

The shell-less chorioallantoic membrane (CAM) assay was carried out by the method of Folkman et al. (R. Crum. S. Szabo and J. Folkman; Science. 230. 1375 is (1985)) as follows: three-day chick embryos were removed from their shells to petri dishes (Falcon 1005) under sterile hood and cultured for further 3 days.

AGM-1470 was dissolved to a 0.45% methylcellulose aqueous solution and aliquots of 10 μl were pipetted onto Teflon rods. After the solution had dried, the methylcellulose disks (about 2 mm in diameter) containing the compound were implanted on the CAM of 6-day embryos.

After culturing for 48-72 hours, formation of avascular zones around the disks was observed with a stereoscope. An avascular zone represents a region in which regression of preexisting vessels has occured.

Percent of avascular zones was calculated by counting the disks forming avascular zones per the total disks tested. In each group there were 12 to 16 embryos.

As shown in Table 4, AGM-1470 showed strong angiogenesis inhibitory activity by the CAM assay.

TABLE 4

| Dose in μg/10 μl methylcellulose | percent of avascular zones |
|---|---|
| 1 | 33 |
| 10 | 62 |
| 25 | 100 |

EXPERIMENTAL EXAMPLE 6

Inhibition of Growth in Established Tumors In Vivo

Using the B16 Mouse Melanoma model described in Folkman et al., Science, 221:719-725 (1983), the angiogenesis inhibitory activity of AGM-1470 was further evaluated. Treatment (Rx) usually started when tumors were approximately 70–100 mm³, approximately 9 to 10 days after inoculation. Tumors were matched for size before inclusion in treated and untreated groups. AGM-1470 was dissolved in isotonic solution by incubating with glass beads and vigorously shaking overnight at 4° C. This preparation was administered subcutaneously at 30 mg/kg every other day.

Tumor growth is presented as a T/C ratio, as defined below. In essence, a ratio equal to "+1" means no inhibition, a ratio equal to "0" means complete suppression of growth, and a negative ratio indicates tumor regression.

$$T/C = \frac{\% \text{ increase in treated tumor volume}}{\% \text{ increase in control tumor volume}}$$

TABLE 5

| B16 Melanoma Model | | |
|---|---|---|
| | T/C Time of Rx: | |
| | 2 wk | 3 wk |
| AGM-1470 | 0.47 | 0.20 |

Day 37 100% untreated dead 50% AGM-1470 treated dead (50% of treated remained alive past day 55)

It was found that the AGM-1470 exerts its inhibitory effects with little or no toxicity; the animals remain active, do not lose weight, and consistently remain free from infection.

What is claimed is:

1. A method for regressing angiogenesis in a mammal, which comprises administering an effective amount of an O-substituted fumagillol derivative or a pharmaceutically acceptable salt thereof to the mammal, wherein the O-substituted fumagillol derivative is a compound of the formula:

wherein $R^1$ is a 2-methyl-1-propenyl or isobutyl group which may be substituted with a substituent selected from the group consisting of hydroxyl, amino, $C_{1-3}$ alkylamino, or di-$C_{1-3}$ alkylamino, and $R^2$ is (1) (i) a carbamoyl group, which may optionally be substituted with from one to two substituents selected from the group consisting of $C_{1-6}$ alkyl, $C_{1-6}$ alkanoyl, chloroacetyl, dichloroacetyl, trichloroacetyl, $C_{1-6}$ alkoxycarbonylmethyl, carboxymethyl, amino, phenyl, wherein the phenyl substituent may be substituted with from one to five substituents selected from the group consisting of $C_{1-6}$ alkyl, $C_{1-6}$ alkoxy, halogen, halo-$C_{1-6}$ alkyl or nitro, naphthyl, benzoyl, halogenated $C_{1-6}$ alkyl, di-$C_{1-6}$ alkylamino-$C_{1-6}$ alkyl, $C_{1-6}$ alkanoyloxy-$C_{1-6}$ alkanoyl, $C_{1-6}$ alkanoylthio-$C_{1-6}$ alkanoyl, $C_{1-6}$ alkylthio-$C_{1-6}$ alkanoyl, arylthio-$C_{1-6}$ alkanoyl, di-$C_{1-6}$ alkylamino-$C_{1-6}$ alkanoyl, ammonio-$C_{1-6}$ alkanoyl.halide, $C_{1-6}$ alkoxycarbonyl, phenoxycarbonyl, chloroacetylcarbamoyl, benzoylcarbamoyl, phenylsulfonyl, wherein the phenylsulfonyl substituent may be substituted with from one to five substituents selected from the group consisting of $C_{1-6}$ alkyl, $C_{1-6}$ alkoxy, halogen, halo-$C_{1-6}$ alkyl or nitro, or di-$C_{1-6}$ alkylsulfonio-$C_{1-6}$ alkanoyl.halide, or (ii) a cyclic amino-carbonyl group selected from the group consisting of pyrrolidin-1-yl-carbonyl, piperidino-carbonyl, morpholino-carbonyl, piperazin-1-yl-carbonyl, 4-methylpiperazin-1-yl-carbonyl, 4-ethylpiperazin-1-yl-carbonyl, 4-phenylpiperazin-1-yl-carbonyl or imidazol-1-yl-carbonyl; (2) an alkyl group, which may optionally be (i) substituted with from one to three substituents selected from the group consisting of amino, $C_{1-6}$ alkylamino, di-$C_{1-6}$ alkylamino, nitro, halogen, hydroxyl, $C_{1-6}$ alkoxy, cyano, carbamoyl, carboxyl, $C_{1-6}$ alkoxycarbonyl, carboxy-$C_{1-6}$ alkoxy, or phenyl, wherein the phenyl substituent may be substituted with from one to five substituents selected from the group consisting of $C_{1-6}$ alkyl, $C_{1-6}$ alkoxy, halogen, halo-$C_{1-6}$ alkyl or nitro, or (ii) epoxidized; (3) a benzenesulfonyl group, which may be optionally substituted with from one to three substituents selected from the group consisting of $C_{1-6}$ alkyl and halogen; (4) an alkylsulfonyl group, which may be optionally substituted with from one to three substituents selected from the group consisting of amino, $C_{1-6}$ alkylamino, di-$C_{1-6}$ alkylamino, nitro, halogen, hydroxyl, $C_{1-6}$ alkoxy, cyano, carbamoyl, $C_{1-6}$ alkoxycarbonyl, carboxy-$C_{1-6}$ alkoxy, and phenyl, wherein the phenyl substituent may be substituted with from one to five substituents selected from the group consisting of $C_{1-6}$ alkyl, $C_{1-6}$ alkoxy, halogen, halo-$C_{1-6}$ alkyl or nitro; (5) a sulfamoyl group, which may optionally be substituted with from one or two substituents selected from the group consisting of $C_{1-6}$ alkyl, or phenyl, wherein the phenyl substituent may be substituted with one to five substituents selected from the group consisting of $C_{1-6}$ alkyl, $C_{1-6}$ alkoxy, halogen, halo-$C_{1-6}$ alkyl and nitro; (6) an alkoxycarbonyl group, which may optionally be substituted with halogen; or (7) a phenoxycarbonyl group, which may optionally be substituted with from one to three substituents selected from the group consisting of $C_{1-6}$ alkyl and halogen; or a pharmaceutically acceptable salt thereof.

2. The method according to claim 1, wherein $R^2$ is $C_{1-6}$ alkylsulfonyl.

3. The method according to claim 1, wherein $R^2$ is sulfamoyl which is substituted by $C_{1-6}$ alkyl or phenyl.

4. The method according to claim 1, wherein the O-substituted fumagillol derivative is O-chloroacetylcarbamoylfumagillol.

5. The method according to claim 1, wherein the O-substituted fumagillol derivative is O-carbamoylfumagillol.

6. The method according to claim 1, wherein the O-substituted fumagillol derivative is O-chloroacetylcarbamoyldihydrofumagillol.

7. The method according to claim 1, wherein the O-substituted fumagillol derivative is O-chloroacetylcarbamoyl-6'b-hydroxyfumagillol.

* * * * *